United States Patent [19]
Yamashita

[11] Patent Number: 5,797,976
[45] Date of Patent: *Aug. 25, 1998

[54] METHOD AND COMPOSITION FOR PROMOTING AND CONTROLLING GROWTH OF PLANTS

[76] Inventor: Thomas T. Yamashita, 1094 Clover La., Hanford, Calif. 93230

[*] Notice: The term of this patent shall not extend beyond the expiration date of Pat. No. 5,549,729.

[21] Appl. No.: 795,192

[22] Filed: Feb. 4, 1997

Related U.S. Application Data

[63] Continuation of Ser. No. 682,850, Jul. 12, 1996, abandoned, which is a continuation of Ser. No. 490,351, Mar. 8, 1990, Pat. No. 5,549,729, which is a continuation-in-part of Ser. No. 354,155, May 19, 1989, abandoned, and Ser. No. 242,951, Sep. 9, 1988, abandoned.

[51] Int. Cl.$^6$ ............................................. C05F 5/00
[52] U.S. Cl. ................................... 71/26; 71/11; 71/64.1
[58] Field of Search .................................. 71/11, 23, 26, 71/64.1, 903, 904, 6–8

[56] References Cited

U.S. PATENT DOCUMENTS

| | | |
|---|---|---|
| 2,756,134 | 7/1956 | Novak . |
| 3,353,949 | 11/1967 | Nau . |
| 3,640,698 | 2/1972 | Backlund . |
| 3,753,722 | 8/1973 | Beucler . |
| 3,846,290 | 11/1974 | Raymond . |
| 4,033,745 | 7/1977 | Moore . |
| 4,119,429 | 10/1978 | Lovness . |
| 4,652,294 | 3/1987 | Arnold . |
| 4,952,229 | 8/1990 | Muir . |
| 5,549,729 | 8/1996 | Yamashita ........................... 71/26 |

FOREIGN PATENT DOCUMENTS

| | | |
|---|---|---|
| 0161395 | 11/1985 | European Pat. Off. . |
| 0055986 | 4/1982 | Japan . |

OTHER PUBLICATIONS

Kirk–Othmer, Encyclopedia of Chemical Technology, vol. 10, Third edition (1980) pp. 46–84 (no month).

*Primary Examiner*—Ngoc-Yen Nguyen
*Attorney, Agent, or Firm*—Bozicevic & Reed LLP; Bret E. Field

[57] ABSTRACT

Composition for and method of stimulating growth of plants, e.g. increase in crop production. The composition comprises a carbon skeleton/energy component, typically a sugar or mixture of sugars; a macronutrient component providing the elements nitrogen, phosphorus, potassium and calcium, preferably also magnesium and sulfur; a micronutrient component providing zinc, iron and manganese, preferably also copper, boron, molybdenum and cobalt. The composition also preferably contains a vitamin/cofactor component and an enhancement component. The composition may be in the form of an aqueous solution or in a form suitable for coating seeds or coating pollen. It may be applied as a foliar spray, as a soil amendment, as a root dip or as an injectable solution. Preferably where, for example, it is used as a foliar spray it is applied at intervals at different stages of growth. The method is useful for treating vegetation to promotes plant growth and/or crop production, also for treating pollen, seeds, roots and soil and inhibiting growth of insects and micro-organisms. A formulation including an energy/carbon skeleton component, a macro nutrient component and a micro nutrient component is applied, e.g. in aqueous solution by foliar spraying. This is done in a manner to make optimum use of the inherent ability of vegetation to harvest solar energy and to utilize other sources of energy and carbon skeleton, such that the energy and nutrients applied by the method of the invention is a fraction of the energy and carbon skeleton requirements of the vegetation.

24 Claims, 2 Drawing Sheets

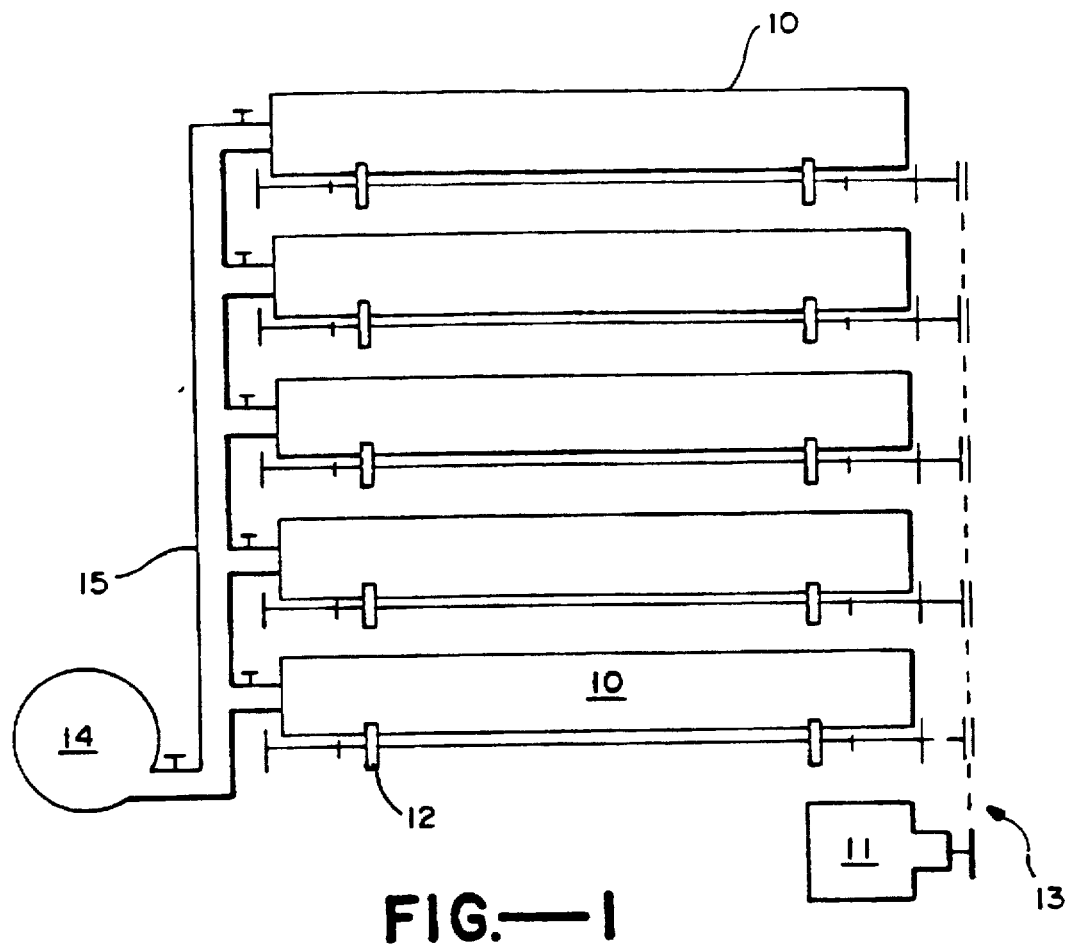
FIG.—1
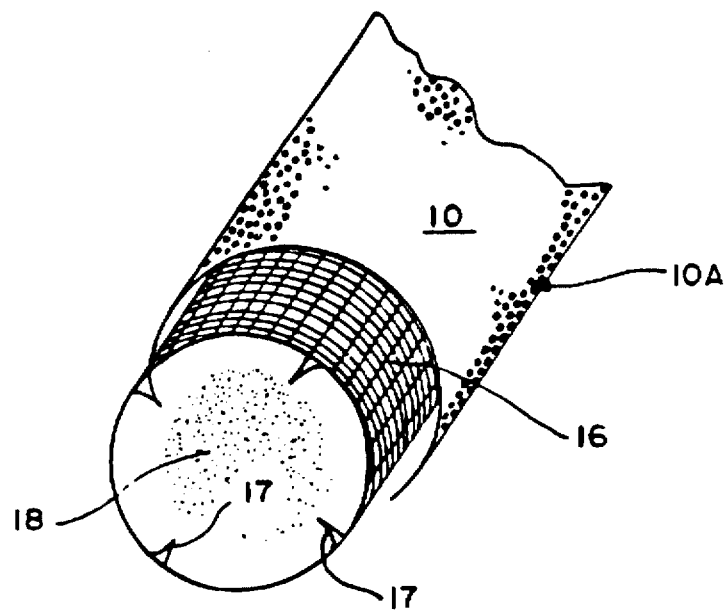
FIG.—2

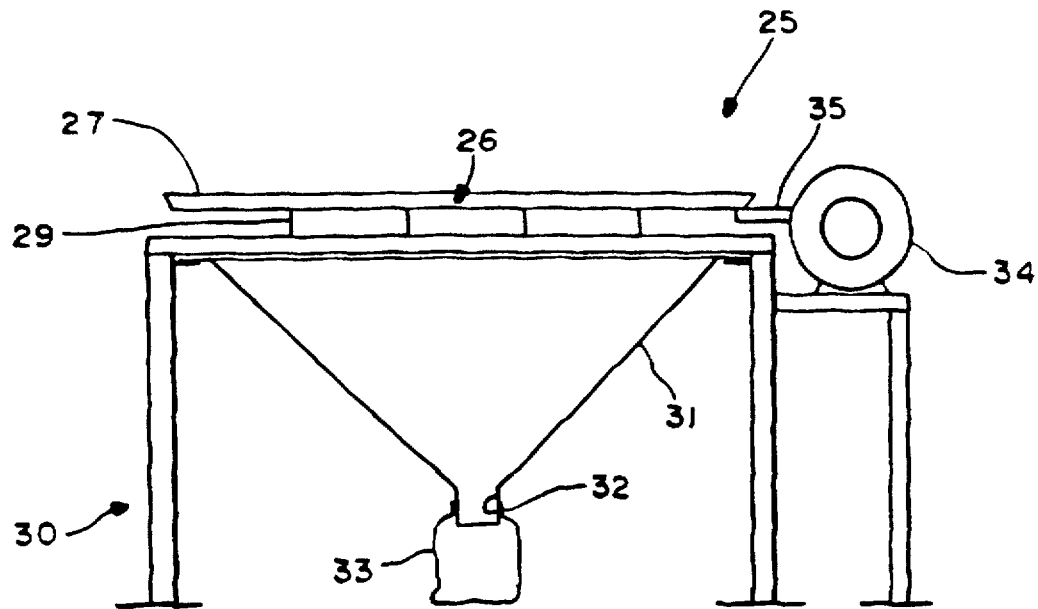
FIG.—3
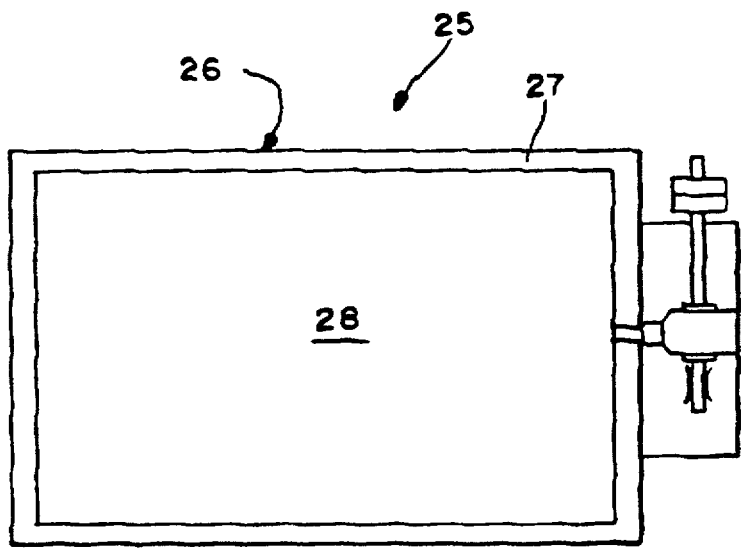
FIG.—4

METHOD AND COMPOSITION FOR PROMOTING AND CONTROLLING GROWTH OF PLANTS

CROSS-REFERENCE TO RELATED APPLICATIONS

This is a continuation of application Ser. No. 08/682,850, filed Jul. 12, 1996 now abandoned, which is a continuation of application Ser. No. 07/490,351, filed Mar. 8, 1990, which has issued as U.S. Pat. No. 5,549,729, which is a continuation-in-part of application Ser. No. 07/354,155, filed May 19, 1989, now abandoned, and application Ser. No. 07/242,951, filed Sep. 9, 1988, also abandoned.

FIELD OF THE INVENTION

This invention relates to a method of treating plants to stimulate their growth and/or their production of edible or other useful products such as fruits, nuts, etc.

BACKGROUND OF THE INVENTION

Traditional plant nutrition has, to date, approached remedial programs through a chronological path of observation, tissue and/or soil analysis, diagnosis, followed by remedy. Such an approach presupposes and accepts certain natural-occurring phenomena as limitations, the realm in which the plant must necessarily function:

(1) that the plant must operate within and as such is constrained by an array of existing environmental factors such as climate and weather, the atmospheric concentration of carbon dioxide (0.03%), duration and intensity of light, the seasons, limiting edaphic factors, etc.

(2) that the plant must obey certain natural "time" frames of growth and reproduction.

(3) that traditional irrigation, fertilization and pest control strategies will express the full potential of a plant's growth and reproduction.

(4) that the application of some predetermined, deficient nutrient(s) at a specified time and rate will restore the plant to its optimal condition.

(5) that the plant is totally resigned to "autotrophism" and as such must conform to this mode of growth, alone.

An example of a current used technique to enhance growth and/or crop production of plants and of its limitations is as follows: Nitrogen added as a fertilizer or plant nutrient may be in the form of pentavalent (oxidized) nitrogen such as a nitrate or in the trivalent (reduced) form such as ammonia or urea. Assuming that the nitrogen applied to a plant is converted to a protein in which the nitrogen is trivalent, if the form of the nitrogen added is a nitrate it must be converted to the trivalent form which requires a considerable expenditure of energy over and above what is required if the nitrogen is applied in the form ammonia or urea. The energy required must come from tissues of the plant directly or through photosynthesis. This would indicate that the application of nitrogen as ammonia or urea would place less demand upon the plant. However the application of nitrogen wholly as ammonia or urea has or may have disadvantages such as:

(1) a sudden drain of both carbon skeletons and energy.

(2) as a result of the condition created in No. 1, a low carbohydrate:nitrogen ratio promoting vegetative but marginal reproductive growth.

(3) inhibition of photosynthetic electron transport by the ammonium ion.

(4) urea-mediated denaturation of proteins through disruption of sulfhydryl bonds.

Another approach is to add a carbohydrate, such as sugar, directly, for example by a foliar spray of a sucrose or other water soluble, assimilable form of carbohydrate. The sugar, when absorbed into the leaves, will provide a source of energy and also a source of carbon skeleton from which, for example, proteins can be synthesized by the plant. This can be, and often is, a very expensive way in which to apply a source of energy and of carbon skeleton. Also if carbohydrate fractions, alone, are added to the plant, various minerals would be needed to compensate for corresponding demands on balanced physiology. Under greenhouse conditions using daily, complete nutrient fertilizers (such as Hoagland's Solution) and a full range of controlled climatic and other environmental factors, the otherwise sudden physiological imbalances brought on by carbohydrate additions alone could be mollified. Resultingly, this would tend to be manifested in increased growth responses. Under actual field conditions, however, these same isolated additions of beneficial carbohydrates would tend to create offsetting physiological imbalances and would not manifest in full the potential benefits of these treatments.

SUMMARY OF THE INVENTION

It is an object of the present invention to provide improvements in the application of nutrients and energy sources to plants especially in consideration of highly variable edaphic and climatic factors, pest and disease pressures and various cultural practices experienced and exercised in both commercial and home-garden farming. Furthermore, presently exercised practices in commercial agriculture, out of economic necessities, place and demand unnaturally productive outputs from the plant. Additionally, all of such vintage productivities are demanded of the plant using traditional, natural cultural practices. It is no wonder then, that farmers are persistently witness to such maladies of the commercial flora as alternate cycles of production, quality variations and shortened productive life, to name a few.

It is a particular object of the invention to provide a method of stimulating the growth of plants and/or the yield of crops or other useful products and to provide compositions which are useful in the practice of such method especially with respect to the aforementioned conditions which beleaguer present day agriculture.

In accordance with the invention there is applied to plants by a suitable route, at suitable times during growth of plants or their crops and at suitable intervals, a composition containing suitable amounts and proportions of the following:

1. Assimilable carbon skeleton/energy component.
2. Macronutrient component.
3. Micronutrient component.

In the preferred CBN composition[1] the following additional components are also present:

1CBN signifies "compensatory balanced nutrition"

4. Vitamin/cofactor component.
5. Enhancement agent component.

A buffer is also used to adjust the pH of the composition.

BRIEF DESCRIPTION OF THE DRAWINGS

FIG. 1 is a diagrammatic top view of drying apparatus;

FIG. 2 is a fragmentary perspective view of one of the drying tubes of FIG. 1 broken away to reveal an interior sleeve;

FIG. 3 is a diagrammatic view of a shake table used to separate pollen grains from anthers; and FIG. 4 is a top plan view of the shake table of FIG. 3.

DETAILED DESCRIPTION OF THE INVENTION

Example 1 below illustrates a composition, sometimes referred to as Bright Sun, which is useful in the practice of the invention.

EXAMPLE 1

Sugar beet molasses was used as stock material and source of energy and carbon skeleton. The total invert sugar (TSI) level was brought to 40% by dilution with water. Following are ingredients used to make the molasses blend:

|  |  | (Elemental) % w/v | Source of Element |
|---|---|---|---|
| Macronutrients |  |  |  |
| Nitrogen | (N) | urea (0.65) KN03 (0.60) total = 1.25% | Urea, Potassium nitrate |
| Phosphorus | (P) | 1.5 | Phosphoric acid |
| Potassium | (K) | 2.0 | Potassium nitrate |
| Calcium | (Ca) | 2.0 | Calcium gluconate |
| Magnesium | (Mg) | 0.5 | Magnesium sulfate |
| Sulfur | (S) | 3.5 | Various sulfates |
| Micronutrients |  |  |  |
| Zinc | (Zn) | 1.0 | Zinc sulfate |
| Iron | (Fe) | 1.0 | Ferrous sulfate |
| Manganese | (Mn) | 1.0 | Manganese sulfate |
| Copper | (Cu) | 0.5 | Cupric sulfate |
| Boron | (B) | 0.02 | Boric acid |
| Molybdenum | (Mo) | 0.03 | Ammonium molybdate |
| Cobalt | (Co) | 0.03 | Cobalt nitrate |
| Vitamins and Cofactors |  |  |  |
| Thiamine | (B1) | 0.02 | Thiamine hydrochloride |
| Riboflavin | (B2) | 0.02 | Riboflavin |
| Nicotinic acid |  | 0.02 | Nicotinic acid |
| Pyridoxine | (B6) | 0.02 | Pyridoxine hydrochloride |
| Folic acid |  | 0.02 | Folic acid |
| Biotin |  | 0.02 | Biotin |
| Pantothenic acid |  | 0.02 | Pantothenic acid (calcium salt) |
| Cyanocobalamin |  | 0.02 | Vitamin B12 |
| Phosphatidylcholine |  | 0.02 | Lecithin |
| Inositol |  | 0.02 | Inositol |
| Para-aminobenzoic acid |  | 0.02 | PABA |
| Enhancement Agents |  |  |  |
| Seaweed extract |  | 2.5% (v/v) | Seaweed extract (cold processed) |
| Citric acid |  | 10.0 gr/gal mix | Citric acid |
| Katy-J Complexing Agent |  | 0.5 gr/gal mix | Katy-J (JKT Corp.) |
| Xanthan gum |  | 0.07 (v/v) | Xanthan gum |
| Sugars and Carbon Skeletons |  |  |  |
| Molasses |  | 40% (TSI) | Beet molasses |
| Buffers |  |  |  |
| Phosphate buffer (pH = 6) |  | 0.02% | Phosphate buffer |

The most important macronutrients are nitrogen, phosphorus, potassium and calcium but it is preferred that the others also be present. The more important micronutrients are zinc, iron and manganese but it is preferred that the others also be present.

The term "Enhancement Agents" used above is intended to include complexing agents, gums and growth regulators. See the discussion below under the caption "Discussion of Components."

Mixing Instructions

While under rapid mechanical or hydraulic agitation, water and two thirds of the total molasses volume are mixed. The amount of added water should represent approximately 15% of the molasses volume. Ingredients are then slowly metered into the batch in the following order:

1. Citric acid
2. Katy-J Complexing Agent
3. Phosphoric acid
4. Nitrogen
5. Potassium
6. Micronutrients (separately)
7. Vitamins and cofactors
8. Seaweed extract
9. Xanthan gum Water is again added to the mix to establish a total invert sugar (TSI) concentration of ~40%. As the TSI of molasses may vary, necessary water volumes may vary accordingly.

As the parent molasses may contain potassium concentrations as much as 2.0–7.0%, it may be necessary to omit potassium nitrate. If potassium nitrate is omitted, the nitrogen may be supplied in total by urea (1.25%). Additionally, inositol levels in molasses may reach levels of 5,800–8,000 ppm, in which case this cofactor may be omitted as well. It is important that the pH of the solution be maintained between 5.0–7.5. This latter requirement may be addressed by analyzing the dilution water sources and adjusting extreme deviations with buffers. Approximately one quart of phosphate buffer per hundred gallons of diluted spray mix (i.e. the "Bright Sun" diluted with water for actual spraying) should meet these needs. If the parent molasses has a pH above 7, the standard addition of citric acid and phosphoric acid will adjust this to a manageable level (most molasses have a pH range of between 5–8).

Storing the material between temperatures of 60–80 degrees F is necessary to prolong the activity of ingredients. Dilutions for actual spray applications should try to achieve a final TSI between 4–10% ("Bright Sun" TSI=40%).

The many crops to be treated may vary in requirements with respect to species, season and an assortment of environmental factors. It would then be necessary to adjust concentrations of the various ingredients. Workable alternative ranges of these concentrations along with alternative sources are presented:

In the above "Katy J" is the trademark of JKT Corporation for a mixture of polyhydroxy organic acids used as a complexing (chelating) agent. Commenting on the enhancement agents, the seaweed extract supplies plant hormones which contribute to regulation of plant metabolism; the citric acid and Katy J serve as complexing or chelating agents and assist in the transport/ingestion of other ingredients of the Bright Sun composition; and the xanthan gum functions as a thickening agent to solubilize ingredients that would otherwise precipitate or drop out.

The phosphate buffer was potassium phosphate.

Instead of, using calcium gluconate as the source of calcium, calcium nitrate $(Ca(NO_3)_2 \cdot 4\ H_2O)$ may be used as it is less expensive. Also it contributes to the nitrogen component, therefore the amount of potassium nitrate will be adjusted.

Table 1 below lists alternative concentrations of the ingredients. It will be understood that the minimal concentrations indicated are not ordinarily employed, greater concentrations being used, each in a significant amount. However, in a given situation a particular ingredient, normally added as such, may be present in another ingredient, e.g. in the water used to dilute the molasses or in one of the other ingredients.

TABLE 1

|  | (Elemental) % w/v |
|---|---|
| Macronutrients | |
| N | 0.000001–20 |
| P | 0.000001–20 |
| K | 0.000001–20 |
| Ca | 0.000001–20 |
| Mg | 0.000001–20 |
| S | 0.000001–20 |
| Micronutrients | |
| Zn | 0.000001–20 |
| Fe | 0.000001–20 |
| Mn | 0.000001–20 |
| Cu | 0.000001–20 |
| B | 0.000001–20 |
| Mo | 0.000001–20 |
| Co | 0.000001–20 |
| Vitamins and Cofactors | |
| Thiamine | 0.000001–5 |
| Riboflavin | 0.000001–5 |
| Nicotinic acid | 0.000001–5 |
| Pyridoxine | 0.000001–5 |
| Folic acid | 0.000001–5 |
| Biotin | 0.000001–5 |
| Pantothenic acid | 0.000001–5 |
| Cyanocobalamin | 0.000001–5 |
| Phosphatidylcholine | 0.000001–5 |
| Inositol | 0.000001–5 |
| Para-aminobenzoic acid | 0.000001–5 |
| Enhancement Agents | |
| Seaweed extract | 0.000001–50 v/v |
| Citric acid | 0.000001–1,000 gr/gal mix |
| Katy-J | 0.000001–1,000 gr/gal mix |
| Xanthan gum | 0.000001–5 w/w |
| Sugars and Carbon Skeletons | |
| Molasses | 0.000001–80% TSI |
| Buffers | |
| Phosphate buffer | 0.000001–5% v/v |

As stated above certain ingredients may contain one or more other ingredients. For example, molasses will often contain some one or more of nitrogen, phosphorus, potassium and calcium, also vitamins and cofactors. Not all of such ingredients are always in the proper form. For example, some or all of the nitrogen may be in the form of proteins and some of the calcium may be in insoluble form.

Table 1A sets forth alternative and preferred ranges of concentrations of ingredients. The composition of Table 1A is for a concentrate or stock solution which would be diluted for use.

RANGE OF PROPORTIONS BRIGHT SUN

TABLE 1A

| A. Carbon Skeleton/Energy Component | 25.00–70.00% |
|---|---|
| B. Macronutrient Component | |
| Nitrogen | 0.30–5.00% |
| Phosphorus | 0.20–5.00% |
| Potassium | 0.30–5.00% |
| Calcium | 0.10–5.00% |
| Magnesium | 0.05–1.50% |
| Sulfur | 0.10–5.00% |
|  | 1.05 30.50 |

TABLE 1A-continued

| C. Micronutrient Component | |
|---|---|
| Zinc | 0.05–2.00% |
| Manganese | 0.05–2.00% |
| Iron | 0.05–2.00% |
| Copper | 0.01–0.10% |
| Boron | 0.004–0.05% |
| Molybdenum | 0.001–0.02% |
| Cobalt | 0.001–0.02% |
|  | 0.166 6.19 |
| D. Complexing Agent(s) | |
| Citric Acid, etc. | 0.005–0.50% |
| Lignosulfonate | 0.005–1.00% |
|  | 0.010 1.50 |
| E. Vitamin-Cofactor Component | |
| Folic Acid | 0.001–0.10% |
| Thiamine | 0.001–0.10% |
| Riboflavin | 0.001–0.10% |
| Nicotinic Acid | 0.001–0.10% |
| Pyridoxine | 0.001–0.10% |
| Biotin | 0.001–0.10% |
| Pantothenic Acid | 0.001–0.10% |
| Cyanocobalamin | 0.001–0.10% |
| Phosphatidylcholine | 0.001–0.10% |
| Inositol | 0.001–0.10% |
| PABA | 0.001–0.10% |
|  | 0.011 0.110 |
| F. Natural Source of Growth Regulator | |
| Seaweed Extract | 0.025–1.00% |
| G. Microbialstat e.g. Proprionic Acid | 0.005–0.50% |
| H. Gum, e.g. Xanthan Gum | 0.0005–0.10% |

It is preferred to remove solids that will not pass through a 60 mesh screen by passing the CSE component successively through 20, 40 and 60 mesh screens and treat the concentrate or stock solution similarly for the same purpose. The pH say range, for example, from 2.5 to 6.5, preferably 3.5 to 5.5. A balance of trivalent and pentavalent nitrogen, e.g. urea and a nitrate, is preferred, e.g. 20 to 80 mols of trivalent nitrogen to 80 to 20 mols of pentavalent nitrogen. This topic (balance of trivalent and pentavalent nitrogen) is discussed below under that heading. The stock solution (and the diluted solution ready for application) if it is stored for a substantial length of time) is preferably stored at 65° to 85° F. Dilution for end use may be to 2.5 to 12.5 percent of CSE but preferably the dilution is to 4.0 to 10.0% of CSE, percentages being by weight based on the solution.

Alternative sources of the ingredients are listed below.
Macronutrients
N-ammonium nitrate, monoammonium phosphate, ammonium phosphate sulfate, ammonium sulfate, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium cyanamide, sodium nitrate, urea, urea-formaldehyde, urea-ammonium nitrate solution, nitrate of soda potash, potassium nitrate, amino acids, proteins, nucleic acids P-superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates X-potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate Ca-calcium ammonium nitrate, calcium nitrate, calcium cyanamide, calcium acetate, calcium acetylsalicylate, calcium borate, calcium borogluconate, calcium carbonate, calcium chloride, calcium citrate, calcium ferrous citrate, calcium glycerophosphate, calcium lactate, calcium oxide, calcium pantothenate, calcium proprionate, calcium saccharate, calcium sulfate, calcium tartrate Mg-magnesium oxide, dolomite, magnesium acetate, magnesium bensoate, magnesium bisulfate, magnesium borate, magnesium chloride, magnesium citrate, magnesium nitrate, magnesium phosphate, magnesium salicylate, magnesium sulfate S-ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine Micronutrients Zn-zinc oxide, zinc acetate, zinc bensoate, zinc chloride, zinc citrate, zinc nitrate, zinc salicylate, ziram Fe-ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate Mn-manganese acetate, manganese chloride, manganese nitrate, manganese phosphate Cu-cupric acetate, cupric butyrate, cupric chlorate, cupric chloride, cupric citrate, cupric gluconate, cupric glycinate, cupric nitrate, cupric salicylate, cuprous acetate, cuprous chloride B-calcium borate, potassium borohydride, borax, boron trioxide, potassium borotartrate, potassium tetraborate, sodium borate, sodium borohydride, sodium tetraborate Mo-molybdic acid, calcium molybdate, potassium molybdate, sodium molybdate Co-cobaltic acetate, cobaltous acetate, cobaltous chloride, cobaltous oxalate, cobaltous potassium sulfate, cobaltous sulfate Vitamins and Cofactors Thiamine-thiamine pyrophosphate, thiamine monophosphate, thiamine disulfide, thiamine mononitrate, thiamine phosphoric acid ester chloride, thiamine phosphoric acid ester phosphate salt, thiamine 1.5 salt, thiamine triphosphoric acid ester, thiamine triphosphoric acid salt, yeast, yeast extract Riboflavin-riboflavin acetyl phosphate, flavin adenine dinucleotide, flavin adenine mononucleotide, riboflavin phosphate, yeast, yeast extract Nicotinic acid-nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile Pyridoxine-pyridoxal phosphate, yeast, yeast extract Folic acid-yeast, yeast extract, folinic acid Biotin-biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolal, 5-(N-biotinyl)-3 aminoallyl)-uridine 5'-triphosphate, biotinylated uridine 5'-triphosphate, N-e-biotinyl-lysine Pantothenic acid-yeast, yeast extract, coenzyme A Cyanocobalamin-yeast, yeast extract Phosphatidylcholine-soybean oil, eggs, bovine heart, bovine brain, bovine liver, L-a-phosphatidylcholine, B-acetyl-g-O-alkyl, D-a-phosphatidylcholine(PTCn), B-acetyl-g-O-hexadecyl, DL-a-PTCh,B-acetyl-g-O-hexadecyl, L-a-PTCh, B-acetyl-g-O-(octadec-9-cis-enyl), L-a-PTCh, B-arachidonoyl, g-stearoyl, L-a-PTCh, diarachidoyl,L-a-PTCh, dibehenoyl (dibutyroyl, dicaproyl, dicapryloyl, didecanoyl, dielaidoyl, 12 diheptadecanoyl, diheptanoyl), DL-a-PTCh dilauroyl, L-a-PTCh dimyristoyl (dilauroyl, dilinoleoyl, dinonanoyl, dioleoyl, dipentadeconoyl, dipalmitoyl, distearoyl, diundecanoyl, divaleroyl,B-elaidoyl-a-palmitoyl, B-linoleoyl-a-palmitoyl) DL-a-PTCh di-O-hexadecyl (dioleoyl, dipalmitoyl, B-O-methyl-g-O-hexadecyl, B-oleoyl-g-O-hexadecyl, B-palmitoyl-g-O-hexadecyl), D-a-PTCh dipalmitoyl, L-a-PTCh, B-O-methyl-g-O-octadecyl, L-a-PTCh, B-(NBD-aminohexanoyl)-g-palmitoyl, L-a-PTCh, B-oleoyl-g-O-palmitoyl (stearoyl), L-a-PTCh, B-palmitoyl-g-oleoyl, L-a-PTCh, B-palmitoyl-a-(pyren 1-yl) hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl Inositol-inositol monophosphate, inositol macinate, myo-inositol, epi-inositol, myo-inositol 2,2' anhydro-2-c-hydroxymethyl (2-c-methylenemyoinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-myo-inositol triphosphate, scyllo-inositol PABA-m-aminobenzoic acid, O-aminobenzoic acid, p-aminobenzoic acid butyl ester, PABA ethyl ester, 3-ABA ethyl ester Complexing Agents Citric acid; Ca, K, Na and ammonium lignosulfonates, fulvic acid, ulmic acid, humic acid, Katy-J, EDTA, EDDA, EDDHA, HEDTA, CDTA, PTPA, NTA.

Growth Regulators

Seaweed extract-kelp extract, kinetin, kinotin riboside, benzyladenine, zeatin riboside, zeatin, extract of corn cockle, isopentenyl adenine, dihydrozeatin, indoleacetic acid, phenylacetic acid, indole ethanol, indoleacetaldehyde, indoleacetonitrile, gibberellins (E.g. GA1, GA2, GA3, GA4, GA7, GA38 etc.)

Gum Components

Xanthan gum-guar gum, gum agar, gum accroides, gum arabic, gum carrageenan, gum damar, gum elemi, gum ghatti, gum guaiac, gum karya, locust bean gum, gum mastic, gum pontianak, gum rosin, gum storax, gum tragacanth Microbialstats Proprionic acid, benzoic acid, sorbic acid.

CSE Components sugar-mannose, lactose, dextrose, arythrose, fructose, fucose, galactose, glucose, gulose, maltose, polysaccharide, raffinose, ribose, ribulose, rutinose, saccharose, stachyose, trehalose, xylose, xylulose, adonose, amylose, arabinose, fructose phosphate, fucose-p, galactose-p, glucose-p, lactose-p, maltose-p, mannose-p, ribose-p, ribulose-p, xylose-p, xylulose-p, deoxyribose, corn steep liquor, whey, corn sugar, corn syrup, maple syrup, grape sugar, grape syrup, beet sugar, sorghum molasses, cane molasses, calcium lignosulfonate sugar alcohol-adonitol, galactitol, glucitol, maltitol, mannitol, mannitol-p, ribitol, sorbitol, sorbitol-p, xylitol organic acids-glucuronic acid, a-ketoglutaric acid, galactonic acid, glucaric acid, gluconic acid, pyruvic acid, polygalacturonic acid, saccharic acid, citric acid, succinic acid, malic acid, oxaloacetic acid, aspartic acid, phosphoglyceric acid, fulvic acid, ulmic acid, humic acid nucleotides and bases-adenosine, adenosine-p, adenosine-p-glucose, uridine, uridine-p, uridine-p-glucose, thymine, thymine-p, cytosine, cytosine-p, guanosine, guanosine-p, guanosine-p-glucose, quanine, guanine-p, NADPH, NADH, FMN, FADH Buffers phosphate buffer-acetate buffer, AMP buffer, calcium tartrate, glycine buffer, phosphate citrate buffer, tris buffer Of the macronutrients listed above, the most important are N, P, K and Ca but this component preferably also includes magnesium and sulfer.

Of the micronutrients listed above, the most important are Zn, Fe and Mn, but this component preferably also includes the others in the list.

Discussion of Balancing Trivalent and Pentavalent Nitrogen

Both trivalent nitrogen, e.g. in the form of ammonia or a compound which is readily convertible to ammonia such as urea, and pentavalent nitrogen such as a nitrate are plant nutrients and sources of the macronutrient N. Trivalent nitrogen in the form of ammonia or urea requires much less energy for assimilation than does pentavalent nitrogen in the form of nitrate. The reduction of nitrate to ammonia using NADH as an energy source requires 198 Kcal per gram mole and further steps in assimilation require approximately 51 Kcal, making a total of about 249 Kcal. If the nitrogen is added in the form of ammonia or urea, an energy saving of about 198 Kcal would be accomplished.

While the use of trivalent nitrogen may appear remedial in conserving the plant's energy load, the application of purely reduced N forms may be harmful. It has been shown that the rapid assimilation of ammonia can place a sudden drain of both carbon skeletons and energy upon the plant. In the presence of abundant carbohydrate reserves, this may not pose a problem. However, the rapidity with which assimilation can occur oftentimes depletes existing reserves to dangerously low levels. This latter physiological state of low carbohydrate:N (CHO:N) ratio may then promote highly vegetative and little reproductive growth. Secondly, the ammonium ion can inhibit photosynthetic electron transport systems. In this latter case, then, sole reliance upon ammonia forms of N can be somewhat toxic to the plant. Urea forms can be quickly converted via urease to ammonia and thus are subject to similar considerations. Additionally, heavy concentrations of urea may act to denature proteins by breaking sulfhydryl bonds and disrupting the tertiary structure of the molecule. If the protein is an enzyme, the denaturation process may potentially disrupt an entire cascade of biochemical reactions.

It is important, then, that a balance between the pentavalent and trivalent forms of nitrogen is maintained during applications to plants. The soil environment offers a degree of buffering due to microbial conversions of ammonia to nitrate forms, but the tri and pentavalent balance is especially important during foliar applications. These ratios preferably range from 10 mols of trivalent N to 90 sole of pentavalent N to 90 solo of trivalent N to 10 close of pentavalent N and most preferably should stay close to a 50:50 ratio. The importance of balanced nitrogen is heightened even more during applications of anions such as phosphates or sulfates, for example, as these require additional energy outlays for absorption. When the nutrients are applied during periods of physiological stress and low metabolic efficiency, then, the plant must literally suffer additional stress. All such factors further emphasize the importance of a carbon skeleton/energy component applied in conjunction as a compensatory factor, providing both energy and carbon skeletons during a critical, physiological, ebb in the life of the plant., Discussion of Components (1) The Assimilable Carbon Skeleton/Energy (CSE) Component The function of this component is to supply carbon skeleton for synthesis of proteins and other plant molecules and to supply energy for plant metabolism. Water soluble carbohydrates such as sucrose, fructose, glucose and other di- and mono-saccharides are suitable, most commonly in the form of molasses or other byproducts of food manufacture. Commercially available lignosulfonates, discussed below under the heading "Complexing Agents," are also suitable as a CSE source inasmuch as they commonly contain sugars. However it is not preferred to use lignosulfonate as a complete substitute for molasses, soluble starch or other carbohydrate because as a foliar spray it has a toxic effect when employed in large amount. For purposes of soil amendment as in Example 8 it may be used as a complete substitute for molasses or other soluble carbohydrate.

(2) The Macronutrient Component

The macronutrients are essential to plant nutrition and growth, to flowering, to flower setting, to fruit setting, to saturation, etc. Preferably all of the macronutrients listed above are present but for short periods of time, or where some of them are present in adequate quantity in the plants or in the soil in which the plants are located, some may be omitted.

The most important macronutrients are N, P and K. The compositions applied in accordance with the invention may omit Ca, S and Mg but preferably they are present.

(3) Micronutrient Component

The most important micronutrients are Zn, Fe and Mn. The others may be omitted but their presence is preferred.

(4) Vitamin/Cofactor Component

The most important are folic acid, biotin, pantothenic acid, nicotinic acid, riboflavin and thiamine. Others may be omitted but their presence is preferred.

(5) Complexing Agents

The function of this component is to solubilize other components of the composition which otherwise may precipitate and become non-assimilable or difficultly assimilable. For example, if the composition is applied as a foliar spray the water will evaporate during daytime resulting in an increase of concentration of macro- and micro-nutrients. At night some or all of the water evaporated during the daytime will be replaced by dew but during the daytime as concentration becomes excessive precipitation may occur. The precipitates are non-assimilable or are difficultly assimilable so their beneficial effect is lost. For example iron present as a micronutrient in the presence of phosphate will form an insoluble phosphate which will precipitate, both elements then becoming non-assimilable.

A complexing agent such as citric acid, humic acids, lignosulfonate, etc. serve to tie up ions such as iron and other ions and prevent them from forming precipitates. In some cases, e.g. with EDTA, this complexing is by way of a process of chelation. The macronutrient or micronutrient so complexed nevertheless remains assimilable.

Supplementing the effect of complexing or chelating agents as more narrowly define above is the CSE component. In an experiment, a one gallon solution approximating the Bright Sun formulation of Example 1 but without a complexing agent was prepared in two ways. In one instance molasses was used as in the formulation of Bright Sun. In another instance water was used in place of molasses. The concentration of other ingredients were the same. The same macronutrients, micronutrients, vitamin/cofactor component and a gum (Xanthan gum) were used in both instances. The molasses was prefiltered through an 80 mesh sieve before mixing with the other ingredients to remove suspended solids. Each solution was stirred for thirty minutes. Then each solution was filtered through an 80 mesh sieve. The solids remaining on the sieve were gently washed with tap water and the remaining solids were dried at 150° F. in an oven. The dried precipitates were weighed.

The weight of solids from the molasses six was 1.30 grams while that from the water (no molasses) six was 6.02 grams, each being derived from a gallon of water.

Since no complexing agent was added in either case, it is apparent that the molasses had a solubilizing effect and inhibited precipitation. Other soluble carbohydrates have the same effect. This may be due to an increase in viscosity caused by the carbohydrate or it may be due in whole or in part to some other effect. It is preferred to use a complexing agent, e.g. Katy-J. citric acid, humic acids, or a lignosulfonate and not to rely solely upon the CSE component alone for the purpose of solubilizing or preventing precipitation of other components.

Following is a general description of the method of the invention following which are Examples 2 to 9.

The rationale of the method of the present invention may be described as follows:

Implementation of CBN Theory requires the following steps:

One needs to calculate the energy units within plant tissues of an hypothetical, superior plant; (e.g., fruits, nuts, supportive tissues). This involves the assigning of a calorie value to carbohydrate (CHO), protein and/or fat constituents; the standard free energy of formation of one gram of CHO or protein is approximately 4.1 Kcal and one gram of fat 9.3 Kcal. In many cases the CHO, protein and fat constitutions of several crops can be obtained from published literature. When these are unavailable, standard laboratory analyses will provide the information needed. Support tissues such as shoots are examined empirically and their mass estimated as approximately 60% of the wet weight. These tissues are all assigned a CHO caloric value as they are almost entirely of cellulitic constitution. Standard procedures for estimating shoot growth is conducted by actual counting of the number of current year shoots on a secondary scaffold. The number of secondary scaffolds are then multiplied by the total number of primary scaffolds. This resultant value is multiplied by the number of shoots originally counted to obtain the total number of new shoots per tree (for smaller plants, the entire plant or a larger fraction can be counted). Ten of the largest sized shoots are removed and their wet weight determined. The average weight is multiplied by the total number of shoots and 60% of this value is used as an estimate of the shoot growth. Shoot growth expressed in grams is then multiplied by 4.1 Kcal to arrive at the energy value of these tissues. Because observations of root growth are difficult, an ideal root:shoot ratio of 0.8 is used to estimate the growth and caloric contribution from the roots (i.e. the energy value of shoot growth is multiplied by 0.8 to obtain the root growth caloric value).

The combined caloric values of reproductive and support tissues now represents the estimated energy units within the hypothetical superior plant.

2. The contribution of the primary macronutrient, nitrogen (N), is estimated from protein constituents (calculated in No. 1 above). To estimate the contribution on N in proteins, the author uses a value of 20%, based upon the N in a typical amino acid, lysine. For example, if almonds are made up of 40% protein, then, one pound of almonds contains 1.3 ounces of N (454 grams of almonds×0.40× 0.20= 36.3 grams=13 ounces). The resultant value is doubled to account for nucleic acids, hormones and related compounds which also contain N. This quantity of N represents an estimate of the minimal annual requirement of N.

3. Quantities of N obtained in No. 2 above are assigned energy of assimilation value. As illustrated in the text, approximately 249 Kcal are required to assimilate one gram molecular weight of N. The nature of N sources (primarily nitrate vs ammonia forms) may alter the kilocalories required for assimilation (249 Kcal required to assimilate nitrate vs 51 Kcal for ammonia) of N. However, energy of assimilation values are derived from biochemical reactions leading up to the incorporating of N into one protein. This does not take into consideration alternate paths of transaminations and/or biochemical transformations. Thus, the author elects to utilize the energy of assimilation values in relation to utilizing nitrate as a sole N source as this is a more realistic estimate of actual energies utilized by a plant in assimilating N.

4. The sums of energy requirements calculated in 1 and 3 above, then, represent the theoretical energy demand for the hypothetical superior plant one hopes to achieve.

5. The solar energy harvesting capacity of the untreated plant is estimated. To obtain this, the following are necessary:

a. estimate of leaf surface area in square meters; the number of leaves are counted from a tertiary or quaternary scaffold (small plants may be counted in their entirety) and multiplied by the appropriate factor; the total number of leaves is multiplied by the area of a typical leaf.

b. 5.78 Einsteins of energy will strike a square meter in one hour; this is equivalent to approximately 250 Kcal/square meter/hour (note: this considers an average sunny summer day).

c. the author uses a 10 hour day and the number of equivalent sunny summer days during the growing season of the plant.

Total leaf surface×total hours×43.2 Kcal/sq. meter/hour are multiplied to obtain the potentially harvestable energy.

6. The Kcal value obtained in No. 5 represents the potential harvestable solar energy. However, actual photosynthetic efficiency of plants runs between 0.5%–3.5%. Percentage designation is based on the following table:

| Maximum Photosynthetic Rates of Major Plant Types Under Natural Conditions | | | |
|---|---|---|---|
| Type of Plant | Appr. P.E.* | Example | Max. Phot.** |
| CAM (Crassulacian acid metabolism) | 0.5% | succulents (*Agave americana*) | 1–4 |
| Tropical, subtropical mediterranean evergreen trees and shrubs; temperate zone evergreen conifers | 1.0% | Scotch Pine (*Pinus sylvestris*) | 5–15 |
| Temperate zone deciduous trees and shrubs | 1.25% | European beech (*Fagus sylvatica*) | 5–20 |

-continued

Maximum Photosynthetic Rates of Major
Plant Types Under Natural Conditions

| Type of Plant | Appr. P.E.* | Example | Max. Phot.** |
|---|---|---|---|
| Temperate zone herbs and C-3 pathway crops | 2.0% | soybean (Glycine wax) | 15–30 |
| Tropical grasses, dicots and sedges with C-4 pathways | 3.5% | corn or maize (Zea mays) | 35–70 |

*Approximate Photosynthetic Efficiency
**Maximum Photosynthesis (mg $CO_2/dm2/hour$) (from: W. Larcher, 1969, Photosynthetica 3:167–198)

Thus, the value from No. 5 is multiplied by the appropriate efficiency to obtain actual harvest solar energy per season.

7. The energy demand (No. 4) is subtracted from the actual harvestable solar energy (No. 6). If the value is negative, this represents a deficit in energy which must be compensated to achieve the hypothetical superior plant.
8. In most cases a deficiency of energy units will have to be compensated with Bright Sun applications. Application programming is based on the following criteria:
    a. early spring growth should be applied as a 4–5% TSI concentration
    b. later growth can be treated with 8–10% TSI solutions
    c. the specific goals of a program will dictate frequency of applications —e.g. if one is trying to overcome alternate bearing in pistachios it is critical that at least 3 applications are applied between early April and mid-May when the shoots bearing next year's fruit buds will be determined; as a general rule, prolog and log phase growth periods are most demanding of energy and nutrients, followed next by the linear and senescence phases as set forth by W. G. Whaley, 1961, in W. Ruhland, ed., Encyclopedia of Plant Physiology, Volume 14, Springer-Verlag, Berlin, pp. 71–112.
9. Most of the carbon skeleton-energy sources such as sucrose and other Bright sun constituents will have entered the plant tissues within 4 days. The author has observed that under spring and summer conditions most plants will manifest noticeable growth 10–14 days following a Bright Sun application. These new tissues not only represent rapidly metabolizing centers, but their relative succulence in combination with this factor facilitate absorption of Bright Sun. It is known that microscopic passage canals, the ectoteichodes, provide communication channels with the outside environment and thus are avenues for absorption of compounds and elements. With the appropriate use of surfactants it may be possible to get materials through the stomata as well. Further, actively transported compounds, which thus require ATP, may gain additional help by the increased oxygen absorption induced by both "salt respiration" and added metabolizable energy units. Nonetheless, taking advantage of rapidly metabolizing, succulent tissues further enhances material absorption and this factor serves as a sound basis for instituting 10–14 day repeat application schedules. Additionally, by 10–14 days localized depletion of elements and/or energy may begin to appear. It is necessary, then, to compensate for the induced increases in metabolism by periodic applications of Bright Sun until the plant is conditioned (about midpoint or further beyond the linear phase of growth) to operate for the remainder of the season at its induced, higher, efficiency level. The more applications per season, the more benefits to the plant. The following table may serve as an example.

Effect of number of sprays with 10% sucrose solution on growth of tomato variety San Jose Extra Early

| No. Sprays | Mean total dry wt/mg | Dry wt increase |
|---|---|---|
| 0 | 188 | — |
| 1 | 204 | 16 |
| 2 | 229 | 41 |
| 3 | 238 | 50 |
| 5 | 281 | 93 |
| 10 | 352 | 163 |
| 20 | 596 | 408 |

Note:
duration of experiment 21 days (from: A.M.M. Berrie, Physiologia Plantarum 13, 1960)

Compensation of deficient energy units is only partly met by a direct addition. That is, let us assume, for example, that a tree requires 100,000 Kcal to produce 25 lbs. of nuts (dry wt.) but can at most harvest 60,000 Kcal of sunlight during the season. If the biological combustion of one mole of sucrose yields 526 Kcal, simple division (40,000 divided by 526=76 moles of sucrose) indicates a need for about 76 moles of sucrose. At 342 grams per mole, direct compensation of energy, then, would require almost 59 lbs. of sugar. Obviously, it would be far too difficult and expensive to add this quantity directly. However, if repeated applications of Bright Sun (5–10% TSI) were practiced at periodic intervals to gradually increase the overall metabolic efficiency and capacity of the plant, the 59 lbs. of sucrose energy would be added indirectly. The addition of sucrose in foliar sprays, for example, is known to improve the plant in a number of ways:

1. delaying senescence
2. increase the number of plastids per cell (including chloroplasts and mitochondria
3. increase thylakoid formation
4. increase thylakoid polypeptides
5. increase cellulose synthesis
6. increase the rate and amount of organic acids secreted by roots, thus improving the ability to extract mineral elements from the soil
7. increase the rate of differentiation of cells
8. stimulate cyclic AMP formation, thus regulating intracellular metabolism leading to increased enzyme activity and overall metabolic efficiency.

Additionally it is known that the application of metal activators, cofactors and coenzymes will not only institute activity of an enzyme but by virtue of the former effect greatly accelerate the rate and efficiency of biochemical reactions. Growth promoting, plant hormones also act in a regulatory capacity and as such can act in a similar fashion. When a full range of factors (as found in Bright Sun) are then used in applications to a plant, the potential voids in one or a number of related factors created by accelerated activity from additions of another are nullified. This is so because of the complete, balanced nature of the Bright Sun mix which will allow compensation of an otherwise deficient factor or factors.

If, for example, one is able to increase the leaf surface area of the given tree by 40%, theoretically, the tree would be able to harvest an additional 24,000 Kcal (60,000 Kcal× 0.40=24,000 Kcal). If the metabolic efficiency of the same tree is improved by 30%, an additional 18,000 Kcal of harvested energy would be possible. The sum of these (24,000 Kcal+18,000 Kcal+42,000 Kcal) or 42,000 Kcal would sore than compensate for the deficiency of 40,000

Kcal (60,000 Kcal+42,000 Kcal=102,000 Kcal, with a requirement of 100,000 Kcal). It is by virtue of these phenomena that a superior plant is produced by treatments of Bright Sun without having to directly compensate an energy deficiency. Rather, it is the combined effects of a minute direct addition along with the all important improvement in overall metabolic efficiency which makes it possible to achieve the status of a superior plant. It is the inclusion of a carbon skeleton-energy source in conjunction with additions of macro and micronutrients, cofactors and coenzymes, growth regulators, complexing agents and related factors that prevents a temporary energy deficit within the plant. That is, energies of assimilation for various elements and compounds are compensated from the beginning of treatment and are not met at the total expense of the plant's reserve energy sources. Thus, a break in metabolic efficiency is avoided and increased rates of metabolism induced by treatments are allowed to continue unimpeded. Under traditional methods of plant nutrition it is not uncommon to create a deficiency or imbalance in the biochemical machinery following treatments with one or more elements.

Compensatory Balanced Nutrition avoids these imbalances by providing a full range of factors at specific ratios designed to promote both growth and reproduction (or growth alone, as with a specific ornamental, e.g.). However, final application scheduling must correlate the benefits to the plant with economic returns to the grower.

The macroscopic manifestations in plants often translates into characters such as increased growth, bud retention, fruit size and quality as well as subtle expressions of tolerance to various fores of environmental stress. A generalized definition of these beneficial factors, then, must emphasize balance and the concepts of "compensatory balanced nutrition". That is, the addition of one factor, such as nitrogen, must take into consideration concomitant needs for energies of assimilation, carbon skeletons to accept nitrogen, the need for cofactors and catalysts and a wide range of other macro and micronutrients. The enhanced rate and activity of a series of biochemical reactions must necessarily create temporary states of deficiency or excess. A "compensatory balances" approach, however, takes all the myriad of factors into consideration. If we were to assign a relative value to these many factors, however, with all else being normal, it is obvious that the energy load of the plant represents the ultimate factor of limitation.

It is the purpose of this patent to emphasize these concepts and to demonstrate the necessity of integrating a "compensatory balanced nutrition" (CBN) of plants. Traditional plant nutrition has to date only addressed the need for various mineral elements. While results say appear to be favorable the potentials have yet to be realized. Rather, by addressing the additional energy requirements and certain key cofactors (such as vitamins) it is possible to achieve growth and production which exceed even the most balanced nutrition of mineral elements.

1. Establish an optimum and/or desired crop level (i.g. tons/acre).
2. Select a plant of superior framework capable of supporting the sass and volume of crop necessary to meet the established optimum crop in No. 1 above.
3. Determine the energy and nitrogen-phosphorus-potassium (NPK)+calcium (Ca)+magnesium (Mg) levels necessary to support all growth during the course of a season for both the plant and crop in No. 1 and 2 above (and also for an average, typical plant). This will include:
   a. All vegetative growth put forth during the current season
   1) roots
   2) shoot growth
   3) increases in girth (expansive growth) for past season growth (e.g. as in tree branches)
   b. All crop tissue (e.g. fruits, nuts, seeds, etc.)
   Note: N, P, K, Ca and Mg levels can usually be obtained from published literature and will be expressed as a percent of dry tissue weight; energy levels are determined from the following:
   c. Carbohydrate (CHO), protein (Prot) and fat constituents making up vegetative and crop growth are determined:
   1) CHO and Prot constituents are assigned a value of 4.1 Kcal/gram
   2) Fat constituents are assigned a value of 9.3 Kcal/gram
   d. Each gram molecular weight of N is assigned 250 Kcal; P, K, Ca and Mg do not receive Kcal designations
4. Determine the energy harvesting capacity of the superior plant in No. 2.
   a. Measure the total leaf surface area of the plant
   b. Establish a photosynthetic efficiency level for the plant (i.e. the ability to harvest incident light energy and to convert it to energy within the plant)
   c. Establish the approximate total energy harvested during the course of a single season (from numbers generated in a and b above)
5. Determine whether or not an energy deficit exists by subtracting the projected, total harvestable energy (in 4c) from the total energy required for the optimum growth and crop (3c and 3d) of the superior plant.
   Note: If energy required for growth and crop (3c and 3d) exceeds harvestable energy (4c), a deficit in energy exists.
6. Determine the energy harvesting capacity of an average, typical plant.
   Note: The format in No. 4 is followed.
7. Determine the degree of energy deficit that exists when comparing energy demands for an optimum crop versus energy harvesting capacity for the average, typical plant in No. 6.
8. The deficit figured in No. 7 represents the immediate in-season energy deficit that must be accounted for to obtain the optimum crop. The deficit figured in 5 represents the energy deficit to be accounted for in succeeding seasons once the superior framework plant is obtained.
9. Determine the predominant form of translocatable carbohydrate in the specific plant as this provides the guideline as to what form of carbon skeleton-energy source will be utilized in Bright Sun[2] for that specific plant.

[2]Bright Sun is the formulation of Example 1

Note: This can be obtained from either published literature or by use of standard laboratory procedures.
10. Based on the specific carbon skeleton-energy source selected, the species specific Bright sun formulation is then applied to the plant and the photosynthetic rate (Pr) monitored daily for 14 days (via $Co_2$ analyzer); the average increase in Pr observed then determines the frequency of applications of Bright Sun necessary to achieve the optimum crop; the following example illustrates this procedure—assume a case as follows:
   (1) The plant is only capable of harvesting 50% of the energy necessary to produce an optimum crop.
   (2) The season is 140 days long (i.e. leading up to harvest).
   (3) The observed average Pr is 300% (i.e. the increase in Pr following each application of Bright Sun).
   (4) If Bright Sun were applied every 14 days (a total of ten applications) a theoretical energy harvest would result in 300% of normal.

(5) If a 50% deficit is the beginning condition, the final energy harvest would more than meet the deficit by a factor of 1.5 (i.e. 1.5 times more energy harvested than would be necessary to just meet the needs for the optimum crop).

(6) Theoretically 0.15 of the optimum crop energy demand would be met with each spray (total of ten sprays).

(7) Thus, to just reach an energy harvest factor of 1.0, approximately seven sprays of Bright Sun would suffice (1.0 divided by 0.15).

(8) If the grower wishes to achieve no more and no less than 1.0 of the required energy demand, a recommendation would be made for seven applications of Bright Sun to be applied every 14 days.

Discussion of Physiological Stress Management

Another approach to the method of the present invention concerns periods of physiological stress in plants.

Plants undergo periods of physiological stress which may have adverse effects on the plants. Such stress periods may be due to normal events such as flowering where the demand for carbohydrates increases and places a demand on the root system of the plant, causing the roots to be depleted of their normal concentration of carbohydrates. Climate may also play a part in stress. For example, if sunlight is below normal during the growing season and photosynthesis is thereby diminished, the plants may have to draw upon their reserves to sustain flowering, flower setting or fruit setting and saturation. Pathogens such as for example verticillium and fusarium, nematodes, etc. or pests such as sites and aphids may also create stress. For example, verticillium and fusarium tend to plug the vascular tissue of plants, thereby preventing absorption of water and resulting in wilting.

Returning to normal phenomena in which at certain stages of normal growth of plants, a physiological stress is imposed, in the case of pistachio trees during setting of the nuts, those nuts which are generally proximal to the main stem of the inflorescence and which are later more commonly abscissed may for a time draw upon the energy reserves of the tree to the detriment of the nuts in more distal positions and it would be better if the abscission of proximal nuts were expedited.

Another example of physiological stress is typified by cotton and other plants with rather massive, luxuriant canopies. Within these canopies, on hot days, the ratio of oxygen to carbon dioxide increases due to plant metabolism. If, as is the case with cotton, the plant is what is known as a carbon 3 plant in which an event in metabolism is the assimilation of carbon dioxide at the alpha carbon of ribulose bis phosphate, oxygen competes with carbon dioxide for this position via a process known as photorespiration. Periods of high light, high temperature and concomitantly higher ratios of oxygen to carbon dioxide favor photorespiration. This results in lowered photosynthetic efficiency as well as both energy and mass accumulation reductions.

Yet another type of physiologically stress may occur where a fertilizer is applied to the soil or to foliage. This fertilizer, especially a nitrate, requires energy for reduction to trivalent nitrogen. In the case of nitrate, this is as such as 198 Kcal per gram molecular weight of N. Energy is also required for assimilation into the plant. While reduced forms of nitrogen (as with ammonia or urea forms) may have lower energy demands for assimilation, the rapidity with which they can be assimilates places a sudden demand on carbohydrates within the plant. Thus fertilization, by virtue of sudden energy and carbohydrate demands, may have a detrimental effect through this additional stress.

Such period of physiological stress may be detected by observation or by analytical methods, via monitoring instruments or they may be predictable on the basis of experience.

It is an important aspect of the present invention that, if a composition of the invention typified by Bright Sun or other suitable formulation described hereinabove is applied before, at the onset of or even during a stress period but before irreparable, unacceptable damage has been done, such application will stimulate the plant and will overcome or ameliorate the effects of stress.

Examples of such stress relief are as follows:

In Example 3 above, the application by foliar spraying of pistachio trees assisted in counteracting the infections of the root systems by *V. dahliae* due to low sugar content of the roots owing to demands made by the plant tissues.

Example 4 illustrates the beneficial effects of such spraying on tomato plants grown in a greenhouse under suboptimal conditions.

Another example of use of the invention to relieve stress is with regard to the matter of the mass of foliage. The greater the mass of foliage and resultant light harvesting capacity, the greater is its ability to carry on photosynthesis. In accordance with the invention a spray of Bright Sun or other composition of the invention is applied when it is observed that the production of energy and mass has dropped or will drop based upon monitoring of net photosynthetic rate and/or predictions based on differences between required and observed mass and energy dynamics. This infusion of the composition of the invention will resuscitate the ability of the plant to increase metabolic efficiency (such as photosynthetic rate) thereby increasing the production of energy and mass.

At critical periods, e.g. flowering, flower set, fruit set, fruit sizing and saturation, stress may be relieved by application of the composition of the invention. The onset of such stress periods may be detected by visual observation, supplemented by or substituted by analytical means such as the LICOR Photosynthesis System described in Example 10 with reference to tomato plants and sugar beets. The LICOR system is an infrared analyzer used to determine carbon dioxide changes and to monitor photosynthesis. The HPLC method referred to in Example 15 measured sugar levels in the roots of olive trees.

Another example of benefit of the invention is a situation where a pathogen causes stress. Verticillium and fusarium colonies plug vascular tissue and prevent absorption of water. A plant can counteract the incipient infection by walling off the pathogen through production of phenylpropanoids, phytoalexins, lignin, suberin, to name a few. The effective defense response requires the immediate production of enzymes, m-RNA and various carbon skeleton-energy compounds. A successful defense response is rate-related, depending largely upon production and placement of the walling off compounds in advance of the pathogens growth through the host. But where, due for example to a period of stress, the plant tissue is low in carbohydrates and energy, this walling off process is impeded. By applying the composition of the invention, for example as a foliar spray, the vigor of the plant is sustained and walling off occurs in advance of the pathogen.

Another example is the effect of site infestation of cotton plants. In California a cotton crop close to roads and subjected to a great amount of airborne dust and laden with mites was sprayed with a composition of the invention two times (2nd spray ca. 2 weeks later) during boll maturation. No ravage by mites was observed whereas the field had a long history of heavy site infestations and damage. Nearby cotton plants not so treated suffered from mite infestation and damage. Additionally the sprayed cotton in dust contaminated areas and elsewhere benefited in the following respects: It did not undergo excessive vegetative (rank) growth, (oftentimes a result of a high nitrogen:carbohydrate ratio) which competes with partitioning of photosynthates to the flowers and bolls. This excessive vegetative growth Interferes with mechanical harvesting of cotton. Nearby cotton which was not so treated grew to a height making it difficult to harvest. The current practice in the cotton industry relies on periodic spraying with a growth regulator to curtail rank growth. However, following applications with the composition of the invention and by virtue of balancing the physiology (low nitrogen:carbohydrate ratio) rank growth was curtailed. An antifungal and antisenescence effect of the composition of the invention was also observed.

In Colorado cantelopes, beans and tomatoes were sprayed with the composition of the invention during flowering and fruit sizing and maturation. In the case of the former two crops, untreated plants succumbed to heavy infections of fusarium wilt whereas sprayed plants remained healthy and productive. Untreated tomato plants senesced and became unproductive following the August harvest while plants sprayed with the composition of the invention remained healthy and productive into the fall months, providing an additional harvest of six tons per acre of tomatoes.

It will therefore be apparent that application of the composition of the invention, for example by foliar spraying before, at the onset of or during stress periods is beneficial.

The following Examples 2 to 9 will further serve to illustrate the invention and several different modes of applying the invention.

EXAMPLE 2—Almond Tree

Three successive foliar sprays on almonds were utilized to help set the young fertilized nutlets. Each spray was spaced approximately 10–14 days apart. The following mixture was used:

| Element | Concentration in Molasses Mix |
| --- | --- |
| Calcium | 1.0% |
| Potassium | 0.6% |
| Zinc | 0.5% |
| Magnesium | 0.3% |
| Nitrogen | 0.7% |
| Phosphorus | 0.3% |
| Manganese | 0.08% |
| Molybdenum | 0.008% |
| Iron | 0.1% |
| Copper | 0.02% |
| Boron | 0.02% |
| Cobalt | 0.02% |
| Thiamine (B1) | 0.01% |
| Riboflavin (B2) | 0.01% |
| Nicotinic Acid | 0.01% |
| Pyridoxine (B6) | 0.01% |
| Folic Acid | 0.01% |
| Biotin | 0.01% |
| Cobalamin (B12) | 0.01% |
| % invert sugars | 40.00% |

The material has assisted in setting the almond crop. The treated blocks have never set a heavier crop in the 17 year history of the ranch. Additionally, as theorized, the use of these molasses sprays in conjunction with materials developed by the author for frost control, contributed towards protecting the almond crop from incurring major damages. While the neighbor blocks sustained total crop losses in excess of 600–800 acres, treated blocks suffered, at most, border damages. This protection occurred under 6–7 continuous hours of 25–26 degrees freezing temperatures.

EXAMPLE 3—Pistachio Trees

At present there are several problems encumbering the pistachio industry: (1) verticillium wilt, (2) alternate bearing, (3) nonsplit of shells, (4) embryo abortion and blanking, (5) nut rancidity, and (6) shell staining. It is the belief of the author, following extensive literary, field and laboratory research, that these maladies are all closely tied to improper plant nutrition. For one, verticillium wilt is caused by an opportunistic soil-borne pathogen. During the period of intensive maturation and nut filling (July and August) the developing crop draws upon all available food reserves. Subsequently, the root system sacrifices much of its reserves and at this time root tip necrosis can be observed. These sites, then, serve as entry points for the pathogen. It is interesting to note that *V. dahliae* falls under the category of a "low sugar pathogen". That is, the organism favors tissues with low concentrations of sugar.

Alternate bearing and related nut quality problems are closely tied to improper nutrition. The calculation of energy flow by the author reveals a deficit in carbohydrates as a primary cause for many of these maladies.

In April the author initiated a foliar spray program to span the months of April through early August (a total of 9 sprays). The purpose was as follows:

1. accelerate the metabolism and upgrade the overall efficiency of the physiological machinery;
2. to add essential elements which not only contribute to goal No. 1, but accounts for and meet the increased demands for these elements;
3. to add energy units and carbon skeletons directly;
4. accelerate abortion of defective nuts at an early stage, thereby leaving the available elemental and energy reserves to perfectly formed healthy nuts;
5. by virtue of No. 4, thin the existing crop and distribute the energy pull of developing nuts over a broader surface;
6. to induce immediate and extensive shoot growth which would give rise to the following year's fruit buds (note: shoot growth and bud differentiation must be completed between the short span of two months, April and May; without it the following year's crop is lost); and
7. to mitigate further infections of verticillium wilt by improving the health of the root system (note: not only does a relatively higher sugar concentration in the root tissue alone reduce the chances for fungal infection but the enhanced rate of root growth allows root tips to literally escape infection as well).

Results of this test thus far are as predicted. Shoot and leaf growth is extensive, measuring anywhere from two to five times the growth seen in neighboring untreated blocks. Defective nuts were aborted 10–14 days in advance of untreated blocks. Shoot growth and concomitant differentiated fruit buds appear very healthy (one can detect this latter condition by observing the size and firmness of the buds). In neighboring untreated blocks many of the fruit buds have abscised, whereas this is not the case in treated blocks. The formulations,

| Element | Concentration in Molasses Mix |
| --- | --- |
| Nitrogen | 1.2% |
| Phosphorus | 1.0% |
| Potassium | 3.6% |
| Calcium | 1.1% |
| Zinc | 0.5% |
| Magnesium | 0.3% |
| Manganese | 0.2% |
| Molybdenum | 0.01% |
| Iron | 0.3% |
| Copper | 0.025% |
| Boron | 0.02% |
| Cobalt | 0.02% |
| Thiamine (B1) | 0.005% |
| Riboflavin (B2) | 0.005% |
| Nicotinic Acid | 0.005% |
| Paraminobenzoic Acid (PABA) | 0.005% |
| Pyridoxine (B6) | 0.005% |
| Folic Acid | 0.005% |
| Inositol | 0.005% |
| Biotin | 0.005% |
| Cobalamin (B12) | 0.005% |
| Katy-J Complexing Agent | 0.5 grams/acre |
| Citric Acid | 10.0 grams/acre |
| % invert sugars | 40.0% |

First two sprays- 40 gpa, 4.0 gpa molasses mix, 2.0 mph ground speed; electrostatic sprayers with 100% delivery from middle three nozzles and 50% delivery from bottom and top nozzles (note: there are five nozzles per half side of sprayer).

Remaining seven sprays- 40 gpa, 8.0 gpa molasses mix, 2.0 mph ground speed; electrostatic sprayers with 100% delivery from middle three nozzles and 50% delivery from bottom and top nozzles.

EXAMPLE 4—Greenhouse Experiment

A greenhouse experiment was established to further test the feasibility of molasses foliar sprays above and in conjunction with the complexing agent, Katy-J. Chile peppers and "Ace" tomato plants of equal size and age were selected (two per treatment) and potted. One set received twice weekly treatments of 1:9 dilution of molasses:water (of the same blend used in pistachio sprays). A second set received the same in combination with one gram per gallon (of molasses mix) of Katy-J Complexing Agent. The plants were placed on the lower deck of a greenhouse table to provide shading of all test plants. This was done to provide a suboptimal environmental condition which would assist in accelerating the expression of any differences as a result of treatments.

To date the tomato and pepper plants sprayed with molasses alone are about 25% larger and those with the added Katy-J Complexing Agent up to 50% larger than control plants. The author feels that Katy-J is an important ingredient in these applications. The complex array and quantity of compounds not only added to but also found in the parent molasses necessitates a complexing agent of superior capabilities. An acid test is the ability of Katy-J to keep the metal elements in solution in the presence of phosphorus and calcium. The agent allows drying of the foliar spray on the leaf surface in a state which can later be rehydrated with atmospheric moisture, thereby extending the period of effective absorption. Further data and photographs on these greenhouse tests are forthcoming.

EXAMPLE 5—Application to Pollen

Preferred Method For Preparing "SUPER SUN POLE"

Closed blossoms are collected mechanically using a standard shaker-catch frame unit. Blossoms are immediately placed through a low rpm shredder, the cutting teeth of which are replaced by two parallel cylinders revolving inward to direct the flow of product. Cylinders are equipped with sheet metal screws (flat tipped with spiral groove on shaft) which extend from the inside of the cylinder wall to the periphery. The axis of the sheet metal screws pass directly through and are perpendicular to the central axis of the revolving cylinder. It is the gentle flailing by these teeth which dislodge mature anthers from the blossoms. A shaking deck and two levels of catch frames (one, a coarse five-mesh screen, the other a solid tin frame) provide a preliminary separation of anthers from expended blossoms. Anthers are further separated from extraneous materials through a shaking deck with three levels: (1) top, a ten-mesh stainless steel screen (sss) ; (2) middle, 20-mesh sss; and (3) bottom, a solid frame. Stamens and larger pieces are removed by the upper screen. Viable anthers fall through the first screen and are caught on the second level. Nonviable dehisced anthers, dust and finer extraneous materials are caught on the lower frame. The motion of the deck action carries product forward. The exit port of each level is staggered to deposit the three classes of material into separate containers. Pure anthers are then dried on racks lined with fine mesh, breathable nylon fabric. A second method for drying, developed by the author involves the use of slowly revolving perforated cylinders. Anthers are placed into a cylindrical 225-mesh nylon sock, which is cut to fit exactly into the inner diameter and length of the cylinder. A gentle stream of chemically filtered air is directed on the revolving cylinder, which along with the gentle tumbling action, facilitate drying. All drying is done in a dehumidified room with temperatures maintained between 18–25 degrees C. An exhaust system, coupled with an air recirculating system keeps a constant, directed mass flow of air through the building. All recirculated air is purified with permanganate filters which removes harmful concentrations of ethylene and aromatics. Drying is completed when pollen reaches 8–10% moisture. This occurs within 24 hours. The pollen and anthers are then placed on the separating table to further refine the product down to pure pollen grains. for most Prunus and Pyrus species, this is accomplished using a 200-mesh stainless steel screen supported by expanded metal. A gentle rubbing dislodges 95–100% of the pollen grains which fall to a catch frame. This pure pollen is either used immediately, placed under short-term storage (0 degrees C.), or placed under long-term storage (−85 degrees C.). Pollen is placed in double, vacuum, heat-sealed plastic bags before storage.

Before being distributed out to the field, the "mild-mannered" pollen grains are processed as follows to attain the level of "SUPER SUN POLLEN":

| Item | Proportion | Source |
|---|---|---|
| Pollen grains | 1.0 part | respective species |
| Powdered sugar | 10.0 parts | powdered sugar |
| Katy-J Complexing Agent | 0.2 part | Katy-J (JKT Corp.) |
| Calcium gluconate | 1.0 part | calcium gluconate powder |
| Yeast extract | 1.0 part | yeast extract |

Procedures for Mixing "SUPER SUN POLLEN"

One part of freshly-processed (or recently removed from cold storage) pollen is first mixed with Katy-J to coat the individual grains. One part each of calcium gluconate powder and yeast extract are then added and likewise agitated (shaken in a large, heat sealable bag) to coat pollen grains. Ten parts of powdered sugar are blended to complete the pollen mix. The finished product should be immediately vacuum, heat sealed (plastic bag) and kept cold at about 0 degrees C. until use. "SUPER SUN POLLEN" is either applied to pollen inserts, sprinkled into the hive and/or applied by aircraft.

Alternate Proportions

| Item | Proportion |
| --- | --- |
| Pollen grains | 1-10 parts |
| Powdered sugar | 1-100 parts |
| Katy-J | 0.000001-10 parts |
| Calcium gluconate | 0.000001-100 parts |
| Yeast extract | 0.000001-100 parts |

Alternate Sources

Katy-J: Katy-J-EDTA mix, lignosulfonates, fulvic acid, ulmic acid, humic acid, hymatomelanic acid, leonardite, citric acid, isocitric acid, EDTA, EDDA, EDDHA, EGTA, HEDTA, CDTA, DTPA, NTA Calcium gluconate: calcium (ca) acetate, ca carbonate, ca cyclamate, ca glycerophosphate, ca heptagluconate, ca ionophore, ca-magnesium, ca-phosphate, ca-succinate, ca-tartrate, ca sulfate Yeast extract: thiamine, riboflavin, nicotinic acid, pyridoxine, folic acid, biotin, pantothenic acid, cyanocobalamin, phosphatidylaholine, PABA (see vitamin and cofactor section for previous "Bright Sun" mix)

Test Results 1.5% water agar (wa) petri plates (five each) were made up as follows:

A—1.5% wa

B—1.5% wa+10% sugar

C—1.5% wa+0.5% calcium gluconate

D—1.5% wa+0.5% yeast extract (cold filtered)

E—1.5% wa+10% sug+0.5% ca gluc+0.5% y ext

Freshly processed pollen grains were lightly sprinkled atop each plate and incubated in the dark for 24 hours. Pollen tube growth was recorded, assigning the A treatment (1.5% water agar, alone) a value of 1 and all others a relative numerical value thereto.

| | Replication | | | | |
|---|---|---|---|---|---|
| Treatment | 1 | 2 | 3 | 4 | 5 |
| A | 1 | 1 | 1 | 1 | 1 |
| B | 19 | 21 | 18 | 21 | 21 |
| C | 7 | 6 | 7 | 5 | 8 |
| D | 5 | 6 | 5 | 8 | 5 |
| E | 23 | 25 | 23 | 24 | 22 |

All blocks on which "SUPER SUN POLLEN" was used show an average crop estimate of 2,200 lbs./acre or better. In some blocks this estimate is close to 3,000 lbs./acre or better. Untreated blocks show average crop estimates all below 2,000 lbs./acre. It is also very pertinent that the treated blocks are carrying the heaviest crop in all the 17 year history of the orchards.

For purposes of aerial application of Super Sun Pollen it is preferred to use a formulation as follows:

| | |
|---|---|
| Pollen grains | 1-10 parts |
| Powdered sugar | 10-10,000 parts |
| Katy-J or calcium lignosulfonate | 0.001-10 parts |
| Calcium gluconate | 0.001-100 parts |
| Yeast extract | 0.001-100 parts |

A typical analysis of yeast extract is as follows. As will be seen it is a source of macronutrients and micronutrients.

EXAMPLE 6—Pest Disruptant

Navel Orangeworm Disruptant, "ASUNDER"

Many insect species are directed to hosts and specific host tissues via olfactory stimuli. The mated female navel orangeworm (*Amyelois transitella Walker*), for example, is attracted to previous year's nuts hanging in the tree (in the spring months) and to the mature nuts. The previous year's nuts or "mummies" which are infested with navel orangeworm(s) (NOW) or other insect larval species (e.g. peach twig borer) are especially attractive to mated females for egg deposition sites.

It has been found that certain fatty acid fractions or crop oils are the key agents of attraction. Foremost among these are the unsaturated fatty acids, linolenic, linoleic and oleic, the latter being most attractive of the three. Crude, unrefined nut and vegetable oils and the acidulated forms of these oils are excellent sources of oleic acid.

During the periods of NOW flight, it may be possible to disrupt the host finding ability of mated females. This is accomplished by permeating the crop environment with attractants that sake it virtually impossible for the female to home in on the host tissue(s). Theoretically, it would be possible to halt a generation and avoid extensive damages to the crop.

In March, 1988, the author conducted several studies on the attractability of various candidate compounds. A two-fold goal was to locate a potent attractant oil and a compound that could be used as a nutrient (with comparable attraction and/or which would not nullify the effects of the oil). Black sticky traps were baited with various compounds and placed into orchards having previous histories of heavy NOW infestations. The number of eggs and moths were recorded for two weeks. The various compounds were as follows: The number of eggs indicates the relative potency of the compounds as attractant.

| Bait | Eggs |
|---|---|
| NOW bait (bran meal) | 23 |
| Soybean meal | 34 |
| 10% Bright Sun | 34 |
| 5% Crude corn oil | 61 |
| Infested mummy nuts (almonds) | 7 |
| 10% Bright Sun + 5% Crude corn oil | 58 |

Wind tunnel studies: 200 mated females were released downwind from the bait in a confined area, 30'×10'×8'; each compound was tested separately for 48 hours each.

| Bait | Females trapped |
|---|---|
| 5% Crude corn oil | 47 |
| Bright Sun | 23 |
| Infested mummy nuts (almonds) | 21 |

Preferred Method for Making "ASUNDER"

| Item | Concentration | Source |
|---|---|---|
| Bright Sun | 55% v/v | Bright Sun |
| Crude almond oil | 40% v/v | Crude almond oil |
| Emulsifier | 5% v/v | Triton X-363M |

Alternate Concentration

| Item | Concentration |
|---|---|
| Bright Sun | 0.000001–75% v/v |
| Crude almond oil | 0.000001–75% v/v |
| Emulsifier | 0.000001–20% v/v |

Alternate Sources

Bright Sun: see alternative mixes in methods for preparing Bright Sun.

Crude almond oil: crude (cd) corn oil, cd cottonseed oil, cd pecan oil, cd sunflower oil, cd walnut oil, cd filbert oil, cd safflower oil, cd olive oil, cd peanut oil, acidulated (ad) almond oil, ad peanut oil, ad olive oil, ad safflower oil, ad cottonseed oil, ad pecan oil, ad sunflower oil, ad walnut oil, ad peanut oil, oleic acid, linolenic acid, linoleic acid, stearic acid, palmitic acid, myristic acid, oleic acid, lauric acid.

Triton X-363M: Bos, Wettal, Pluronic, Plurafac, Iconol, Klearfac, Pluraflo, Armix, Armul, Flomo, Alipal, Blancol, Emulphogene, Emulphor, Gafac, Igepal, Daxad, Agrimul, Hyonic, Monolan, Nopalcol, Atlox, Atphos, Atplus, Atsurf, Brij, Myrj, Renex, Span, Tween, Compex, Pestilizer, Toximul, Surfonic, T-Det, T-Mulz, unimuls, Upanals, Sponto, Atplus 300 F, Lecithin.

Field Test

In May, 1988, the author conducted a large scale field test. Aerial applications were split with one half of the scheduled volume per acre applied on alternate passes. Two weeks later the remainder of the materials were applied to the rest of the fields. During this period and through three weeks into June, 1988, NOW females and eggs were trapped at random locations throughout the treated and untreated blocks. There were 17 traps altogether (both egg traps and moth sticky traps). The results are summarized in the following table:

| Treatment | Maximum No. Eggs for one week | Maximum No. Moths for one week |
|---|---|---|
| Control | 134 | 16 |
| "ASUNDER" | 23 | 1 |

Note:
Control figures represent the readings from five traps; ASUNDER readings were taken from 12 traps; all trapping figures represent the maximum catches for one week over a duration of seven weeks.

Proportions of ingredients may vary from the proportions given under the heading "Preferred Method for Making ASUNDER" as follows:

| Bright Sun | 30–70% v/v |
|---|---|
| Crude Almond Oil | 15–50% v/v |
| Emulsifier | 1–10% v/v |

EXAMPLE 7—Frost Damage Inhibition

Frost Control: "SUNBURST"

Frost concerns represent one of the limiting factors in plant agriculture. Many liquids, including water, can be supercooled below the melting point of the solid phase. Freezing occurs thereafter either spontaneously or in the presence of a catalyst. The catalysts are often referred to as ice nuclei, the two general types of which are classified homogeneous and heterogeneous. Homogeneous nuclei are important below −10 degrees C., while heterogeneous nuclei come into play above this range. Of primary importance to agriculture are freezing temperature ranges between −5 to 0 degrees C. It is at these temperatures that many plant tissues are damaged. That is, supercooling does not occur due to the presence of nuclei catalyzing the liquid to solid transition.

Within this initial freezing range of −5 and 0 degrees C., it has been found that three primary epiphytic bacterial species serve as ice nucleation catalysts (*Pseudomonas syringae*, ps. *fluoresecens*, *Erwinia herbicola*). The bacteria are normal inhabitants colonizing the plant surfaces. It is believed that certain constituents located on the cellular membrane initiate ice formation bringing about freezing and plant tissue damages. Resultingly, programs directed at reducing the populations of ice nucleation bacteria have provided a significant degree of frost protection. Three general avenues of achieving these goals are via the use of:

1. bactericides
2. ice nucleation inhibitors
3. antagonistic bacteria

These approaches relate to findings of a log-linear relationship between frost injury to plants (at a specified temperature) and the quantity of ice nuclei associated with the plant. The lower the population of ice nucleation bacteria, then, the sore opportunity for supercooling in the absence of ice formation.

Of the three methods, the use of antagonistic bacteria offers a highly viable and economical means of achieving frost protection. It exercises the principles of microbial ecology of the phylloplane. The soil environment has multiple niches and buffer zones, which contribute to ecological diversity. However, the phylloplane has fewer dimensions and resultingly its extent of diversity is more with respect to time or seasons. An epiphytic bacterial species which aggressively colonizes surface tissue, then, encounters few natural obstacles other than variations of moisture and temperature. Thus, once started, a particular colony can be difficult to displace. A logical approach, then, would be to introduce large populations of antagonists following:

1. previous natural decline of ice nucleating species
2. bactericidal applications to reduce ice nucleating species To date investigators have overlooked two key factors for successful introduction of an antagonistic bacterial species:

1. conditioning the antagonist
2. providing a temporary substrate on plant surfaces for expansion and an interim for adaptation. The methods developed by the author address these issues.

Preferred Method for Preparing "SUNBURST"

The previously outlined preferred "Bright Sun" is diluted in the mixing tanks and/or spray rig tank to which is added fermentation and/or plate cultures of naturally occurring antagonists isolated from plant surfaces. The bacteria are not genetically altered but were isolated by the author from almond bud wood. It is a naturally occurring, commonly found species which lives epiphytically on various species of plants. The population is diluted to a concentration of about one billion colony forming units (cfu) per milliliter of dilute spray mix.

Conditioning of the organisms is accomplished by including 0.4% V/V of Bright Sun into the fermentation tank substrate (8 gr/L nutrient broth) or petri plate medium (23 gr/L NA). Subsequently, the spraying of Bright Sun not only serves as a carrier but coats plant surfaces with a temporary substrate for initial colonization. Bright Sun also provides the growing plant with substantial quantities of various nutrients. With an optimal growth status the plant is capable of exuding more of the bacterial growth promoting organic acids and related nutrients.

The following organisms can be used:

1. Pseudomonas fluorescens (antagonistic strain T-1)
2. Pseudomonas putida (antagonistic strain K-1)

Results of Field Tests

| 2-88 | |
| --- | --- |
| Bright Sun | 4 gpa |
| Ps. fluorescens T-1 | ~1 billion cfu per ml |
| phosphate buffer | 1 qt. per 100 gallons mix |
| Spray volume | 80 gpa |
| 3-88 | |
| Bright Sun | 4 gpa |
| Phosphate buffer | 1 qt. per 100 gallons mix |
| Spray volume | 80 gpa |
| Bright Sun | 4 gpa |
| Ps. fluorescens T-1 | ~1 billion cfu per ml |
| Phosphate buffer | 1 qt. per 100 gallons mix |
| Spray volume | 80 gpa |

Readings following two consecutive days at approximately 3.3 degrees C. (six hours each morning):

Untreated —43 of 60 randomly selected nuts damaged

"SUNBURST"—7 of 60 randomly selected nuts damaged

The frost struck in late May, 1988. Areas which were subjected to similar periods of −3 to −4 degrees C. freezing temperatures and which normally sustain yearly damages exceeding 50% losses are holding crops in excess of 2,000 lbs. per acre. Neighboring untreated plots which were subjected to these temperatures sustained more than 80% frost damage.

EXAMPLE 8—Soil Amendment

Soil Amendment: "MORNING SUN"

Continued productivity of our unparalleled agricultural lands faces grave challenges. The basic natural resource and foundation of agriculture, the soil on which we raise our crops, is undergoing chemical and/or physical deterioration over the many years of cropping. Secondly, world expansion and urbanization into otherwise productive locations necessitates development of many virgin lands. However, through the natural processes of geological weathering, these unchartered soils are virtually sterile and unfit for growing profitable crops.

Foremost among soil maladies are salt accumulations and build ups of toxic elements. Furthermore, economical, large scale farming has necessitated the extensive use of herbicide stripping on the effective radius of root growth. Without periodic replenishment of organic matter to these areas, various problems of soil compaction, water penetration and mineral tie up intensify over time. Almost all irrigated regions do not have proper central drainage facilities nor drainage water desalting and recycling plants. Consequently, growers will often take drainage run off, six this with their irrigation water sources recycling and accumulating salts on their cropland. Aside from establishing efficient drainage and drainage water treatment plants, many growers may improve the quality of the reclaimed marginal croplands with proper soil management.

A central theme of any effective soil management program relies on maintaining the organic matter and thus microbial fractions of the soil. Several species of microbes can harvest atmospheric nitrogen, for example. Under ideal conditions, an entire ecologically coordinated, yet diverse, group of microbes can improve the soil in a myriad of ways:

1. improve structure through formation of aggregated particles
2. increase water retention and availability to roots
3. increase the overall and rate of water drainage
4. improve soil aeration
5. increase the availability of otherwise soil-bound macro and micronutrients
6. add nitrogen to the soil
7. increase the rate of conversion of ammonia forms to nitrates
8. reduce electrical conductivity
9. increase the ion exchange capacity of the soil
10. buffer the plant roots from harmful and toxic levels of chemicals and/or elements
11. degrade harmful chemicals
12. reduce populations of soil-borne plant pathogens and/or reduce the opportunity for their pathogenesis.

The following soil amendment six addresses these needs:

Preferred Method for "MORNING SUN"

| Item | Concentration | Source |
| --- | --- | --- |
| Part I Mix: | | |
| Bright Sun | parent mix | Bright Sun |
| Katy-J Complexing Agent | 5 gr/gal mix | Katy-J (JKT Corp.) |
| Part II Mix: | | |
| Gloeocapsa sp. | 1 trillion cfu per gallon mix | fermentation cultures of |
| Streptomyces griseus | 1 trillion cfu per gallon mix | fermentation cultures of |
| Gleocladium roseum | 1 trillion cfu per gallon mix | fermentation cultures of |
| Bacillus subtilis | 1 trillion cfu per gallon mix | fermentation cultures of |
| Pseudomonas fluorescens | 1 trillion cfu per gallon mix | fermentation cultures of |
| Cellulase | 2,500 units/gal | Type VII from Penicillium funiculosum |
| Alpha amylase | 36,000 units/gal | Type XA from Aspergillus oryzae |
| Glycerol | 2 qt./gal | glycerol |
| Buffer | 8 oz./gal | phosphate buffer |
| Zinc sulfate | 0.05% w/v | zinc sulfate |
| Manganese sulfate | 0.05% w/v | manganese sulfate |
| Iron sulfate | 0.05% w/v | Ferrous sulfate |

The alga species, Gloeocapsa, is cultured in one-half strength Hoagland's Solution supplemented with one gram per 100 gallons six of Katy-J. The culture suspension is aerated and provided with constant lighting (via submersible incandescent lamps with an output of light equivalent to approximately 2.0 Einsteins of light energy per square meter per hour). Approximate duration of incubation is 5–7 days. All culturing is conducted under aseptic conditions.

*Gleocladium roseum, B. subtilis, S. griseus* and *ps. fluorescens* are cultured in fermentation tanks similar to that for Gloeocapsa but without lighting and with a different substrate. Nutrient broth (8 gr/L) is supplemented with Bright Sun (0.4% v/v). *Pseudomonas fluorescene* is a fast grower and is generally mature within 48 hours culturing time. The remaining three species require a minimum culturing period of 72 hours and in many cases 120 hours. All operations are conducted aseptically, under constant, low aeration and at 25 degrees C.

When mature, the cultures are aliquanted and blended with glycerol, phosphate buffer and enzymes. They are placed in breathe-cap containers and refrigerated immediately (5 degrees C.). Application involves delivery through the irrigation system or comparable means of approximately one gallon Part I Mix+1 quart part II Mix per acre (rate may vary with soil condition).

Alternative Concentrations

| | |
|---|---|
| Part I Mix: | |
| Bright Sun | see original text on Bright Sun |
| Katy-J | 0.000001–20 gr/gal |
| Part II Mix: | |
| Gloeocapsa sp. | 1.0–10(20th) cfu/gal |
| *S. griseus* | " |
| *B. subtilis* | " |
| *Ps. fluorescens* | " |
| *G. roseum* | " |
| Cellulase | 1.0–10,000 units/gal |
| a-amylase | 1.0–75,000 units/gal |
| glycerol | 1.0–90% v/v |
| Buffer | 1.0–10% v/v |
| Zinc sulfate | 1.0–20% w/v |
| Manganese sulfate | 1.0–20% w/v |
| Iron sulfate | 1.0–20% w/v |

Alternate Sources

Part I Mix: (see original text on Bright Sun)

Part II Mix:

Gloeocapsa sp.: Anabaena sp.

*S. griseus: S. aureofaciens*

*B. subtilis: B. megaterium, B. cereus, B. brevis*

*Ps. fluorescens: Ps. putida*

*G. roseum: Tallaromyces flavus, Trichoderma viride, T. harzianum*, Penicillium, citrium, *Acremonium falciforme, Ulocladium tuberculatum*

Cellulase:

Type I (*Aspergillus niger*),

Type II Type (*A. niger*),

Type V (*T. viride*),

Type VI (*T. viride*) from *T. fusca* a-amylase:

Type IA (porcine pancreas),

Type IIA (Bacillus sp)

Type XI-A (Bacillus sp.)

Type VI-A,

Type VII-A (porcine pancreas),

Type VIII-A (barley malt)

Glycerol: glycerol

Buffer: see original text on Bright Sun Zn, Mn and Fe sulfates: see original text on Bright Sun.

Field Test

Application of one gallon per acre of "MORNING SUN" mixes were made on 160 acres of pistachio trees, heavily infested with microsclerotia of *Verticillium dahliae* (150 cfu/gram soil). Eight inch soil cores (1" diameter) were removed from the drip line of five randomly selected trees before and after (2 months) treatment. The soil was air dried, pulverized and the five replicates blended. A 10 gram aliquant was then suspended in 100 ml sterile water. A 1 ml aliquant was removed and plated on 1.5% water agar, allowed to air dry overnight, sealed with parafils, then placed under two weeks of dark incubation (25 degrees C.). Colony forming units (cfu) were read following the two week incubation.

| Replicate | cfu before treatment | cfu after treatment |
|---|---|---|
| 1 | 6 | 3 |
| 2 | 2 | 1 |
| 3 | 4 | 4 |
| 4 | 3 | 1 |
| | 15 cfu | 9 cfu |

% reduction = 40%

The following composition is useful for the same purpose as the composition of Example 8 but is intended for use without adding micro-organisms. It relies upon natural flora in the soil:

| | |
|---|---|
| CSE Component | 5.0–75.0% |
| Nitrogen | 2.0–15.0% |
| Phosphorus | 1.0–15.0% |
| Potassium | 2.0–6.0% |
| Calcium | 0.1–15.0% |
| Zinc | 0.1–3.0% |
| Manganese | 0.1–3.0% |
| Iron | 0.1–3.0% |
| Vitamins | 0.0–0.5% |
| Complexing Agent(s) | |
| Citric Acid | 0.01–1.0% |
| Calcium lignosulfonate | 5.0–75.0% |

NOTE:
The higher proportion of calcium ligno-sulfonate would be used where it also serves as the CSE component.

NOTE: The higher proportion of calcium lignosulfonate would be used where it also serves as the CSE component.

EXAMPLE 8A—Soil Treatment Tests

Use of Morning Sun for soil treatment is recommended for soils which are one or more of the following: (1) alkaline, (2) high in salts, (3) high in clay; also soils which have one or more of the following properties: (4) slow infiltration rates, (5) are low in organic matter, (6) are infertile due to minerals being tied up and unavailable for assimilation, (7) are infested with disease inocula.

Alkaline soils are benefitted by microbial activity stimulated by Morning Sun, such activity acting to reduce pH and also to generate a mucilage which is a good soil conditioner.

Soils high in salts benefit from the increase in infiltration rate caused by Morning Sun.

With regard to clay, the texture of clay is altered by such microbial activity, becoming more granular. This in turn leads to enhanced infiltration rates. Due to such microbial activity, organic matter is also increased which benefits the soil.

Where the soil is infertile due to tying up of minerals, the complexing agent, especially lignosulfonate, solubilizes minerals and makes them available to plants.

With regard to disease inocula, Morning Sun stimulates the growth of antagonists.

Experiments were carried out Sep. 2–Nov. 10, 1989 as follows: Morning Sun was applied at the rate of 0.1 gallon on each of two 400 square foot plots and was applied with about 1100 gallons of water.

Random samples of soil from the treated plots, likewise random samples of soil from adjacent untreated plots, were examined by standard technique to determine microbial counts.

The soil was also evaluated by standard techniques for soil aggregation and for infiltration rates. Results are summarized as follows:

| Microbial Counts Treated | Control |
|---|---|
| 164 | 11.25 |

Each figure is the mean of four samples.

| Soil Aggregate Tests Treated | Control |
|---|---|
| 2 | 5 |

These are mean values of four samples each and indicate degree of cloudiness of the air dried soil swirled in water. Less cloudiness indicates more aggregation of the soil.

| Infiltration Test Treated | Control |
|---|---|
| 0.45 inch per hour | 0.15 inch per hour |

These figures indicate greater infiltration/permeability of the treated soil.

EXAMPLE 9—Coating and Root Di

The soil environment presents a complex range of integrated factors promoting and/or inhibiting plant growth and reproduction. Foremost among the many influential factors is the nature and density of the microbial populations. From the very moment of sowing or planting, the seed or plant roots become enveloped in the dynamic flux of various soil-borne organisms and directly and/or indirectly are affected in subsequent growth. Cultural practices, nature, the basal soil chemistry and microbial populations interact to either favor or impede growth. Various soil-borne pathogens, for example, are opportunistic, gaining entry and/or establishment during weakened states of plant development. Generally speaking, then, adjustments of the soil environment favoring rapid growth and suppressing soil-borne pathogen colonization would subsequently provide opportunity for optimum seed germination, stand, growth and reproduction of the commercial crop.

In recent years a growing awareness of soil ecology has prompted investigations into the science of soil amendments directed towards these ends. Goals have been achieved through modifications of various edaphic factors which would favor growth of existing beneficial populations, by the direct addition of beneficial organisms and a combined effort of both. Supplementary introductions of beneficials have targeted both edaphic enhancing forms as well as antagonists of plant pathogens. The additions of soil amendments has resulted in rather consistent benefits but in large-scale practice has proven to be somewhat cost-limiting. Conversely, the supplementing of antagonists and other beneficials has been met with inconsistencies in results.

The author has explored the nature of these observed phenomena in an attempt to explain inconsistencies and to design cost effective solutions. Invariably, investigators exploring the introduction of beneficials have overlooked the need for concomitant additions of agents which would enhance their establishment. Secondly, those who have taken the approach of adding soil amendments have done so with primary regard to introducing the end product of ideal microbial activity. Such an approach necessitates massive additions and/or displacement of existing soil. Rather, the author has approached soil improvement whereby minor improvements in certain key edaphic parameters in combination with the introduction of ecologically interrelated populations would achieve near ideal growing conditions. The concept rests heavily upon anticipating a gradual reconstruction of the soil by virtue of timely sequential increases in specific microbial populations. For example, species which can harvest and assimilate nitrogen gas would be a first priority for enhancement. As these populations increase and die off they would provide a substrate for following species. These would add mass and beneficial by-products of their growth such as mucilage, which assists in soil aggregation and thus water penetration, aeration and the release of otherwise bound elements.

Practical avenues for instituting these concepts center about:

1. the addition of bulk volumes of organic matter
2. irrigation drenches with microbial suspensions
3. irrigation introductions of chemicals and/or elements enhancing the chemical and/or microbial environment
4. the coating of seeds and/or roots prior to or during planting.

The author will integrate the above approaches and attempt to exercise their combined virtues via production of the superior seed coating and/or root dip treatment, "SUN COAT".

Preferred Method for Producing "SUN COAT"

| Material | Ratio or Concentration | Source |
|---|---|---|
| Bright Sun | 10% v/v | Bright Sun |
| Algin | 2% w/v | Keltone LV |
| Bentonite Clay | 4% w/v | Bentonite Clay |
| Buffer | 25 mM | 25 mM K2HPO4 25 mM KH2PO4 |
| Katy-J | 2 gr/gal mix | Katy-J Complexing |
| Agent | | |
| *Bacillus subtilis* | 4 × 10(12th) cfu/gal | plate/ fermentation cultures |
| *Pseudomonas fluorescens* | 4 × 10(12th) cfu/gal | plate/ fermentation cultures |
| *Bacillus thuringiensis* | 4 × 10(12th) cfu/gal | plate/ fermentation cultures |
| *Gliocladium virens* | 4 × 10(10th) cfu/gal | seed/plate cultures |

Gliocladium virens is first cultured on boiled wheat seeds using the following procedure:

| | |
|---|---|
| wheat seeds | 1 cup |
| Bright Sun | 2 oz. |
| water | 14 oz. |

The seeds are foiled for approximately 40 minutes then transferred to sterile trays. After cooling, a spore suspension (ca. $1 \times 10^6$ th/ml) is sprayed onto the wheat seeds. Trays are protected with a transparent cover which allows air exchange and incubated at 26 degrees C.+ low light intensity for approximately 10–14 days. Incolum is collected by placing the spore-covered wheat seeds into a strainer. While agitating, a gentle stream of water is run over the seeds to dislodge spores. The collected spore suspension is then added to the sun Coat mix. *Bacillus subtilis, B. Thuringiensis* and *Pseudomonas fluorescens* are cultured in fermentation tanks with the following media:

| | |
|---|---|
| Nutrient Broth | 10 grams/L |
| Yeast Extract | 10 grams/L |
| Bright Sun | 20 ml/L |
| Phosphate Buffer | 20 mM |
| Water | 1 L |

The ingredients are brought to a boil then autoclaved in flasks at 15 psi, 121 degrees C. for 25 minutes. Large-scale operations may replace autoclaving with the use of ultraviolet (UV) lamp sterilizers. The media is first boiled in a concentration about twenty times that of actual usage. It is then diluted with water to the appropriate levels before being pumped through the UV sterilizing unit. The sterilized media is transferred from the UV sterilizer to fermentation tanks equipped with sterile aeration units. Starter cultures of the organisms are grown in shake culture flasks 48 hours prior to their inoculation into fermentation tanks. All cultures are kept at 26 degrees C. and under low light intensity. Pseudomonas fluorescens requires 24–49 hours culturing, while *B. subtilis* and *B. thuringiensis* may require 72–120 hours.

The parent Bright sun is then diluted with the suspensions of *G. virens, B. subtilis, B. thuringiensis* and *Ps. fluorescens*. Additional water is added to obtain a 10% v/v Bright Sun mixture. To the final diluted mix the following are added:

| | |
|---|---|
| Katy-J | 2 grams/gal |
| Buffer | 16.7 grams K2HPO4/gal |
| | 13.2 grams KH2PO4/gal |
| Bentonite Clay | 4% w/v |
| Algin | 2% w/v |

During the mixing, it is important to dilute the Bright Sun as far as possible before adding the culture suspensions so as to avoid osmotic stresses on the organisms. Bentonite clay and algin must be added gradually and mixed under high shear agitation to avoid clumping.

The seed to be coated should be soaked and disinfected through a 10% bleach solution for approximately two minutes then immediately and thoroughly rinsed free of bleach with water (this step may be optional depending upon the nature of natural infecting flora). Disinfected seeds are then dipped into the Sun Coat six, allowed to drain, and placed upon drying trays lined with breathable fabric. A gentle stream of air (not exceeding 35 degrees C.) is directed on the seeds to expedite their drying. After about 30 minutes the seeds are placed into a tumbler which individualizes any clumping which had occurred during seed drying.

Alternate Concentrations

| Material | Ratio or Concentration |
|---|---|
| Bright Sun | 1.0–50% |
| Algin | 0.1–10% |
| Bentonite Clay | 0.1–15% |
| Buffer | 0.001–1 M |
| Katy-J | 0.1–50 grams/gal |
| *Bacillus subtilis* | 10 – 1 × 10–25th cfu/gal |
| *B. thuringiensis* | 10 – 1 × 10–25th cfu/gal |
| *Pseudomonas fluorescens* | 10 – 1 × 10–25th cfu/gal |
| *Gliocladium virens* | 10 – 1 × 10–25th cfu/gal |

Alternate Materials

Bright Sun—see text under Bright Sun Algin—Xanthan gum, guar gum, gum agar, gum accroides, carboxymethyl cellulose, methyl cellulose, starch, Pelgel, Methocel, gum arabic, gum carragaenan, gum damar, gum elemi, gum ghatti, gum guaiac, gum karya, locust bean gum, gum mastic, gun pontianak, gum rosin, gum storax, gum tragacanth Bentonite Clay—montmorillonite clay, kaolinite clay, illite clay, amorphous clay, sesquioxide clay, chlorite clay, vermiculite clay, peat, talc, nu-Film 17

Buffer—succinic acid, malonic acid, hydroxylamine, histidine, cacodylic acid, EDTA (versene), B,B'-dimethylglutaric acid, maleic acid, carbonic acid, citric acid, 4 or 5-hydroxymethylimidazole, pyrophosphoric acid, phosphoric acid, imidazole, 2-aminopurine, ethylenediamine, 2,4,6 collidine, 4 or 5-methylimidazole, triethenolamine, diethylbarbituric acid, tris-(hydroxymethyl) amino-methane, glycyglycine, 2,4 or 2,5-dimethylimidazole, acetate buffer, calcium tartrate, phosphate citrate Katy-J—see alternatives to Katy-J under Bright Sun *Bacillus subtilis—B. cereus, B. pumilus, B. mycoides, B. megaterium, Thiobacillus ferrooxidans, Actinoplanes missouriensis, A. utahensis*, Micromonospora spp., *Amorphosporangium auranticolor, Streptomyces griseus, S. aureofaciens, Clostridium butyricum, Glomus mosseae, Bacillus thuringiensis*—as above Pseudomonas fluorenscens—Ps. putida, Enterobacter cloacae, Alcaligines spp., *Erwinia herbicola, Agrobacterium radiobacter, Rhizobium japonicum, R. leguminosarum, Serratia liquefaciens, Arthrobacter citreus, A. crystallopoietes, A. globiformis, Pasteuria penetrans, Azotobacter chroococcum, A. paspali, Klebsiella pneunoniae*, Nitrosomonas spp., Nitrobacter spp.

*Gliocladium virens—G. roseum, Chaetomium globosum, Penicillium oxalicum, P. funiculosum, P. urticae, P. vermiculatum, Trichoderma harzianum, T. hamatum, T. Viride, T. koningii, Fusarium moniliforme* variety subglutinans, *Pythium nunn, P. oligandrum, Laetisaria arvalis, Coniothyrium minitans, Arthrobotrys amerospora, A. conoides, Acremonium boreale, A. falciforme, Typhula phacorrhiza, Hyphochytrium catenoides, binucleatae Rhizoctonia solani, Talaromyces flavus, Sporodesmium sclerotivorus, Dactylella oviparasitica, Verticillium lacanii*, Azolla spp., Gloeocapsa spp., *Beauveria bassiana, Ulocladium terculatum*

The specific nature of soil-borne diseases and/or edaphic factors encountered with a particular crop and geographical setting necessitates appropriate adjustments in the organisms and/or ingredients selected in Sun Coat. For this reason, the strains and recipe listed under "preferred methods" represent as close as possible an ideal "general" Sun Coat.

Secondly, seed coating is but one aspect of Sun Coat. The product can also be modified and used as a root dip and/or included with the planting water. A suggested form for the latter two cases is as a powdered product. Excluding the organisms, Bright Sun, algin, bentonite clay, buffer and Katy-J are blended with a minimal volume of water then spray dried. The organisms are cultured and spore-forming species induced to sporulate. These are freeze dried into a powder form and subsequently blended with the spray-dried six.

Commenting further on this example, the bentonate clay and the algea function to adhere the composition to the seeds and to the roots. The added Katy-J assists in germination of the coated seeds and is helpful in promoting proliferation of desired micro-organisms in both seed and root treatment. In application of the composition to roots of seedlings to be planted, it is preferred to prepare a dry mixture of the spray dried mixture described above and of the freeze dried micro-organisms in the proportions described above. This dry mixture may be shipped to and stored by the farmer who may then mix it with water and dip the roots of seedlings in the resulting aqueous product just before planting. The micro-organisms are beneficial in seed germination and plant growth.

Alternatively, the spray dried mix may be used without the addition of the freeze dried micro-organisms, in which case the spray dried product will stimulate the growth of beneficial micro-organisms naturally present in the soil.

EXAMPLE 10 Nematode Effect of Composition of the Invention on Tomato Plants and Sugar Beet Plants in a Greenhouse Sugar beets (*Beta yulgaris*) and tomatoes (*Lycopersicon esculentum*) were planted in pots and grown in a greenhouse under identical conditions with exceptions described below.

In the case of sugar beets the sugar beet cyst nematode (*Heterodera schachtii*) was added at approximately 2500 invasive stage (J2) larvae per pot. In the case of tomatoes root-knot nematodes (*Meloidogyne javanica*) were added at approximately 2500 invasive stage (J2) larvae per pot.

The sugar beets and tomato seedlings were transplanted to six inch diameter clay pots using a 1:3 parts mixture of white sand:river sand. Initially all plants were set up on a drip system delivering nutrient solution until the plants had regained health from transplanting. One week prior to testing all plants were taken off of the nutrient solution and were watered twice daily with deionized water. Even, diffused lighting was obtained by suspending a single layer of cheesecloth on the interior of the greenhouse.

Certain of the plants of each species were treated as described below with Bright Sun and others (controls) were not so treated.

In the case of the treated plants the stock spray material (the Bright Sun formulation) was diluted as needed to achieve a nitrogen concentration of 1200 parts per million. Spray was delivered with a household plant misting bottle to undersides and tops of foliage. Parameters set on the LICOR Photosynthesis System followed standard procedures with the use of a quarter liter chamber, twenty cubic centimeters per second air flow and stomatal leaf resistances of one. Readings were taken per chronology chart. Bright Sun was formulated as described in Example 1 above except that corn syrup was used instead of sugar beet molasses.

Corn syrup was used for the following reason: In long term field application to crops as in Examples 2 and 3 above, the brown residue effect described below is not significant. The "brown residue effect" results from the use of molasses which leaves a brown residue on the foliage which may act as a light impedance and may offset photosynthesis measurements. In long term field usage this brown residue effect is diminished because of absorption of the residue by plant tissues and because growth of the plant tissues dilutes the effect. In short term, greenhouse experiments the brown residue-light impedance effect is more significant. For that reason corn syrup was used instead of molasses because it is clear and transparent and causes little or no brown residue effect.

In the Bright Sun formulation calcium lignosulfonate was used as a complexing agent and supplementary carbon skeleton-energy source, a xanthan gum thickening agent, KELFLO, was also used and 0.3% proprionic acid was used as a microbialstat. The procedure set forth in Example 1 was substantially followed. This constituted a stock solution which was diluted as described above for spraying.

The plants (both tomatoes and sugar beets) treated with Bright Sun produced such more vegetative growth than the controls.

EXAMPLE 11 Pollenation of Olive Trees by-Aerial Spraying

A block 1,000 acres in size of olive trees in California were treated by aerial spraying with a Sun Pollen consisting of the following ingredients in the proportions given below.

| Powdered sugar | 122 parts by weight |
|---|---|
| Calcium gluconate | 23 parts by weight |
| Yeast extract | 23 parts by weight |
| Pollen | 10 parts by weight |

Two applications were made by aerial dusting, each in the amount of 178 grams per acre, one application being on Apr. 22, 1989 and the other on Apr. 25, 1989.

The treated block produced a substantially greater crop than untreated trees in the same orchard.

EXAMPLE 12 Alfalfa

In several cases crops were treated by foliar spraying of Bright Sun. In one case the foliar spraying occurred following the second cutting and resulted in a 25% increase in yield by the third cutting and a substantial increase in protein content. Also the treated plants reestablished much more quickly and with sore density in the fall. In another case two sprays of Bright Sun at the rate of 2 gallons per acre increased yield by 36%.

EXAMPLE 13 Cotton

Cotton crops in Mississippi, Texas, California were sprayed with Bright Sun, in one case during boll maturation, in another during flower set and boll set, in another case during boll set saturation. In all cases substantially greater yields of cotton resulted.

EXAMPLE 14 Tomatoes

In one case in California Bright Sun was applied by aerial spraying 2 gallons per acre in mid and late June. In another case in California Bright Sun was applied twice by aerial spraying to 20 acres at the rate of 2 gallons per acre. In both cases substantially improved yields resulted. In Colorado a single spray during bloom of tomatoes intended for hand picking and canning resulted in the plants producing an additional 10 tons per acre, larger tomatoes, increased solids, sore even ripening and larger size.

EXAMPLE 15 Verticillium Wilt As A Stress Factor

This example illustrates the physiological stress caused by *Verticillium dahliae* and is typical of stress caused by many pathogens and of the natural resistance of plants to such pathogens.

*V. dahliae* is an opportunistic soil borne pathogen, as are numerous other pathogens. Almost all plant species have some degree of multigene resistance to *V. dahliae* and other soil borne pathogens. Such defense mechanism localizes the pathogen to the site of entry by the production of "walling off compounds" This resistance response by the host plant requires, among other things, the following:

1. increased carbohydrates
2. more ATP and precursors for phenylpropanoids, phytoalexins, lignins, suberin and related "walling of compounds"
3. increased rates of glycolysis
4. increased rates of pentose phosphate pathway due to increased demands for precursors, nucleic acid and NADPH
5. increased enzyme production (thus, increased m-RNA)
6. increased mitochondrial biogenesis
7. increased transport of furanoterpenes from the noninfected to infected regions Furthermore, it has been found that several of the new mitochondria formed during marginal plant resistance responses develop cyanide insensitive respiration (beginning at a point after ubiquinone in the oxidative phosphorylation chain). As a result, there is beat produced at the expense of little to no ATP energy production. Research has shown that the deficient mitochondria may be products of phospholipid-deficient membranes. Thus, it may be hypothesized that reactions leading up to and following synthesis of fatty acids, glycerol, acetyl coenzyme-A, NADH, FADH2, NADPH and ATP, all of which are factors contributing to optimum metabolisms of the plants, are ever more important in the resistance a 15 response.

It is most interesting to note that the increase in root disease incidence in time is closely correlated to the onset of flowering of many plant species. Not only do flowers serve as photosynthetic sinks but rates of metabolism, including respiration in the tops of the plant, are known to increase markedly during these periods. Infections by root pathogens may occur with less difficulty at these times as a successful resistance response on the part of the plant would be hampered by a competition for both energy and substrate from flower formation.

A major factor in reducing verticillium wilt is to institute a full range of programs designed to improve and maintain plant health as follows:

1. improve soil aeration and water drainage
2. improve mineral nutrition (quantity and balance)
3. improve pruning practices
   a. maximize sunlight (thus, photosynthetic efficiency)
   b. maximize leaf:fruit ratios
4. improve irrigation
   a. low volume, slow delivery to avoid standing water
   b. even depth of penetration
   c. avoid stress, especially during critical periods
5. improved ground working to avoid cutting and wounding of roots
6. avoid frost, insect and disease damages In the final analysis there is the simple balancing of the equation:

Mass+energy produced by the plant during the season is equal to or greater than

Mass+energy found in the crop and vegetative growth

In more detail, all factors contributing towards maximizing plant health (especially during the onset of wilt infection, or in general, stress periods) will minimize verticillium wilt. The successful resistance response is a rate-dependent response. That is, the faster reactions take place to produce compounds needed to wall off the pathogen, the &ore chance there is for a successful resistance response. Several ramifications contained in Optimal Rate of Metabolic Reaction can be implied from the following reaction velocity equation:

v=velocity of reaction
Kp=catalytic rate constant
Km=Michaelis Constant (concentration of substrate at which half-maximal velocity is reached)
[S]=substrate concentration
[E]=enzyme concentration $$v = \frac{Kp}{\left(1+\frac{Km}{[S]}\right)} [E]$$

That is, all factors contributing towards increasing photosynthetic(s), enzyme concentration |E| and enzyme activity (Kp) maximize the resistance response.

As a practical demonstration of the principles stated above, the sugar levels in roots of olive trees in an olive orchard were measured as follows: 1–3 mm diameter roots were removed from the north side of the trees, all samples being taken at a 1 to 2 foot depth. They were washed in tap water and were submitted to a laboratory for analysis of sugars, the most significant of which was maltose, which is the immediate hydrolysis product of starch. Maltose is then converted in the roots to glucose which is transported to the upper parts of the tree. The trees thus sampled included healthy heavy cropped (i.e. having a heavy crop of olives indicated in the following table as HHC), healthy noncropped (HNC) trees whose roots were afflicted with verticillium wilts (DV), trees whose limbs were afflicted with olive knot (DOK), weak heavy cropped (WRC) and weak noncropped (WNC). The roots were analyzed by high performance liquid chromatagraphy (HPLC). Maltose analyses were as follows:

| | |
|---|---|
| HNC | <0.05% |
| HNC | <0.05% |
| DV | 2.65% |
| DOK | 2.50% |
| WHC | 5.83% |
| WNC | 1.50% |

Percentages are based on dry weight.

The high concentrations of maltose in the roots of the diseased and weak trees indicated that an excessive demand was being placed on the starch reserves of the root systems. The low concentration of maltose in the roots of the healthy trees indicated a normal condition in which no excessive demand is placed on the starch reserves of the roots.

Apparatus suitable for processing of pollen as described above in Example 5 is shown in FIGS. 1 to 4.

Referring now to FIGS. 1 and 2 a number of perforated cylinders 10, for-example five in number, are provided which are suitably supported in horizontal position parallel to one another and are rotated about their longitudinal axes by a motor 11, rubber disks 12 bearing against the tubes and suitable connecting means indicated generally as 13 so that the tubes are rotated at a suitable speed, for example 15 to 30 rpm. An electric fan and heater 14 blows heated air through a manifold 15 and into the ends of the tubes 10. Preferably the air is maintained in a suitably dehumidified condition and at a suitable temperature, for example a moisture content of 20 to 40 relative humidity and a temperature of 18 to 25 degrees C. For example, the apparatus may be operated in a dehumidified room and the air is preferably treated chemically, for example by contact with potassium permanganate to eliminate potentially harmful substances such as ethylene and aromatics which are produced by organic material such as the anthers which are being treated, such material being harmful to the pollen.

Referring now to FIG. 2, one of the cylinders 10 including its perforations 10A is shown and is broken away to reveal an inner sock or sleeve 16. The sock 16 is formed by stitching four segments of material together and is then turned inside out so that the unions 17 project inwardly to act as louvers to agitate and tumble the anthers which are shown at 18. The sock 16 is fixed to the interior surface of the cylinder 10 by any suitable means.

The sock 16 may be made of 225 mesh nylon, although other materials may be used and the mesh size will vary according to the species of anthers.

The duration of this drying will van from case to case, a 24-hour period being typical. The dried anthers are then removed from the cylinders 10 and are placed on a shake table 25 which is shown in FIG. 3. The drying process may be carried out continuously rather than batchwise.

Referring now to FIGS. 3 and 4, the shake table 25 comprises a tray 26 having a rim 27 and a perforated bottom 28 supported by flexible members 29 on a frame 30. A funnel 31 is supported by the frame 30 beneath the tray 26 and at its lower end the funnel is fitted with a spout 32 over which a bag 33 may be slipped. A motor 34 is supported on the frame 30 and is connected by a reciprocating connector 35 to the tray 26. The bottom 28 of the tray is perforated, being conveniently formed by wire mesh screen having a mesh size such as to pass the liberated pollen grains but to hold back the remnants of the anthers left after crushing them to release the pollen grains. A suitable mesh size for anthers of almonds is about 170 mesh.

The motor 34 is operated to shake the tray at a suitable oscillatory speed, for example 400 to 500 cycles per minute. Meanwhile the anthers are gently rubbed by hand or by means of brushes, the pressure being sufficient to break open the anthers to liberate the pollen grains but insufficient to damage the pollen grains. The shaking action causes the pollen grains to fall through the screen 28 as they are released from the anthers, thereby limiting damage to the pollen grains due to the rubbing action.

The pollen may be processed and used as in Example 5 immediately or it may be stored, for example at 0 degrees C., for short periods of time or at at −85 degrees C. for long periods of time.

Further processing of the pollen is preferably carried out as described in Example 5.

The following is a list of crops to which the invention is applicable. The compositions applied are listed under Product and are applicable to each of the crops under a particular heading. Rates are gallons per acre or quarts per acre except in the case of the seed coating, Sun Coats.

Legend:
a=Bright Sun
b=Morning Sun
c=Super Sun Pollen
d=Asunder
e=Sun Burst
f=Sun Coat

| Crop | Product | Rate | Applications |
|---|---|---|---|
| Cereal: | | | |
| Rice (*Uryza sativa*) (*Zizania aquatica*) | | | |
| Wheat (*Triticum aestivum*) | a | 1–5 gpa | 3–6 |
| Corn (*Zea mays*) | b | 1–4 qt/a | 2–4 |
| Barley (*Hordeum vulgare*) | f | — | 1 |
| Oats (*Avena sativa*) | | | |
| Sorghum (Sorghum bicolor) | | | |
| Rye (*secale cereale*) | | | |
| Millet (various genera) | | | |
| Legumes | | | |
| Soybean (Glycine max) | | | |
| Peanut (*Arachis hypogaea*) | | | |
| Beans (Phaseolus spp.) | | | |
| Broad Bean (*Vicia faba*) | a | 1–5 gpa | 3–7 |
| Pea (*Pisum sativum*) | b | 1–4 qt/a | 2–4 |
| Chickpea or Garbanzo (*Cicer Arietinum*) | f | — | 1 |
| Black Eyed Pea (*Vigna sinensis*) | | | |
| Lentil (Lens spp.) | | | |
| Pigeon Pea (*Cajanus indicus*) | | | |
| Guar (*Cyamopsis tetragonoloba*) | | | |
| Forage Crops: | | | |
| Alfalfa (*Medicago sativa*) | a | 1–5 gpa | 5–9 |
| Clover (Trifolium spp.) | b | 1–4 qt/a | 2–4 |
| Bird's Foot Trefoil (*Lotus corniculatus*) | c | 1–5 gr/a | 1–3 |
| Vetch (Vicia spp.) | f | — | 1 |
| Sweet Clover (Meliolotus spp.) | | | |
| Lespedeza (Lespedeza spp.) | | | |
| Lupine (Lupinus spp.) | | | |
| Sorghum-Sudan (Sorghum spp.) | | | |
| Kentucky Bluegrass (*Poa pratensis*) | a | 1–3 gpa | 3–5 |
| Bromegrass (*Bromus spp.*) | b | 1–4 qt/a | 2–4 |
| Timothy (*Phleum pratense*) | f | — | 1 |
| Orchardgrass (*Dactylis glomerata*) | | | |
| Fescua (Festuca spp.) | | | |
| Bermudagrass (Cynodon spp.) | | | |
| Dallisgrass & Bahiagrass (Paspalums spp.) | | | |
| Ryegrass (Lolium spp.) | | | |
| Bentgrass (Agrostis spp.) | | | |
| Stem and Leaf Crops: | | | |
| Sugar Cane (*Saccharum officinarum*) | | | |
| Artichoke (*Cynara scolymus*) | | | |
| Asparagus (*Asparagus officinalis*) (note: repeated application in asparagus may allow more Spring cuttings) | | | |
| Broccoli (*Brassica oleracea*) | | | |

| Crop | Product | Rate | Applications |
| --- | --- | --- | --- |
| Brussels Sprouts (*B. oleracea*) | a | 1–5 gpa | 4–7 |
| Cabbage (*B. oleraces*) | b | 1–4 qt/a | 2–4 |
| Celery (*Apium graveolens*) | f | | |
| Chard (*Beta vulgaris*) | | | |
| Chinese Cabbage (*Brassica campestris*) | | | |
| Collards (*B. oleracea*) | | | |
| Endive (*Cichorium endivia*) | | | |
| Kohlrabi (*B. oleracea*) | | | |
| Lettuce (*Lactuca sativa*) | | | |
| Parsley (*Petroselinum sativum*) | | | |
| Rhubarb (*Rheum rhaponticum*) | | | |
| Spinach (*Spinacia oleracea*) | | | |
| Root Crops: | | | |
| Potato (*Solanus tuberosum*) | | | |
| Cassave (*Manihot esculenta*) | | | |
| Sweet Potato (*Ipomoea batatas*) | | | |
| Beets (*Beta vulgaris*) | | | |
| Taro (*Colocasia* spp.) | | | |
| Carrot (*Daucus carota*) | | | |
| Horseradish (*Rorippa armoricia*) | a | 1–5 gpa | 3–9 |
| Jerusalem artichoke (*Helianthus tuberosus*) | b | 1–4 qt/a | 2–4 |
| | f | — | 1 |
| Onion (*Allium cepa*) | | | |
| Parsnip (*Pastinaca sativa*) | | | |
| Radish (*Raphanus sativus*) | | | |
| Rutabaga (*Brassica napobrassica*) | | | |
| Salsify (*Tragopogon porrifolius*) | | | |
| Turnip (*Brassica rapa*) | | | |
| Yam (*Diascorea* spp.) | | | |
| Fruit and Seed Vegetables: | | | |
| Tomato (*Lycopersicon esculentum*) | a | 1–5 gpa | 3–9 |
| Eggplant (*Solanum melongena*) | b | 1–4 qt/a | 2–4 |
| Curcurbits (various Curcurbitacea) | f | — | 1 |
| Okra (*Hibiscus esculentus*) | | | |
| Pepper (*Capsicum* spp.) | | | |
| Fruit and Nut Crops: | | | |
| Citrus (*Citrus* spp.) | | | |
| Grape (*Vitis vinifera*) | | | |
| Banana (*Musa* spp.) | | | |
| Apple (*Malus* spp.) | | | |
| Stone Fruits (*Prunus* spp.) | | | |
| Blueberry (*Vaccinium* spp.) | | | |
| Brambles (*Rubus* spp.) | | | |
| Cranberry (*Vaccinium macrocarpon*) | | | |
| Currant (*Ribes sativum*) | | | |
| Pear (*Pyrus communis*) | | | |
| Avocado (*Persea americana*) | | | |
| Cashew (*Anacardium occidentale*) | | | |
| Coconut (*Cocos nucifera*) | a | 4–15 gpa | 3–9 |
| Date (*Phoenix dactylifera*) | b | 1–4 qt/a | 2–4 |
| Fig (*Ficus carica*) | c | 1–5 gr/a | 1–4 |
| Guava | d | 4–15 gpa | 1–2 |
| (*Psidium guajava*) | | | |
| Litchi (*Litchi chinensis*) | e | 4–15 gpa | 2–3 |
| Maracuja (*Passiflora* spp.) | f | as a root dip during planting | |
| Mango (*Magnifera indica*) | | | |
| Olive (*Olea europea*) | | | |
| Papaya (*Carica papaya*) | | | |
| Pineapple (*Ananas comosus*) | | | |
| Pomegranate (*Punica granatum*) | | | |
| Almond (*Prunus amygdalus*) | | | |
| Brazil Nut (*Bertholletia excelsa*) | | | |
| Filberts (*Corylus* spp.) | | | |
| Macadamia (*Macadamis ternifolia*) | | | |
| Pecan (*Carya illinoensis*) | | | |
| Pistachio (*Pistacia vera*) | | | |
| Walnuts (*Juglans* spp.) | | | |
| Sunflower (*Helianthus annus*) | | | |
| Beverage Crops: | | | |
| Coffee (*Coffea arabica*) | a | 4–12 gpa | 3–9 |
| Tea (*Thea sinensis*) | b | 1–4 qt/a | 2–4 |
| Cacao (*Theobroma cacao*) | f | as a root dip during planting | |
| Cola (*Cola nitida*) | | | |
| Hops (*Humulus lupulus*) | | | |
| Oil, Fat and Wax Crops: | | | |
| Safflower (Carthamus spp.) | | | |
| Coconut (*Cocos nucifera*) | | | |
| African Oilpalm (*Elaeis Guineensis*) | | | |
| Castor Bean (*Ricinus commuis*) | | | |
| Rape (*Brassica* spp.) | a | 1–5 gpa | 3–6 |
| Sesame (*Sesame indicum*) | b | 1–4 qt/a | 2–4 |
| Sunflower (*Helianthus annus*) | f | — | 1 also as a root dip on selected crops |
| Linseed (*linum usitatissimum*) | | | |
| Tung (*Aleurites* spp.) | d | 1–5 gpa | 1–3 |
| Soybean (Glycine max) | | | |
| Carnauba (*Copernica cerifera*) | | | |
| Candelilla (*Euphorbia antisyphilitica*) | | | |
| Jojoba (*Simmondsia chinensis*) | | | |
| Spices, Perfumes and Flavorings: | | | |
| Black Pepper (*Piper nigrum*) | | | |
| Cinnamon (*Cinnamomum zeylanicum*) | | | |
| Clove (*Eugenia caryophyllata*) | | | |
| Vanilla (*Vanilla planifolia*) | | | |
| Mint (*Mentha* spp.) | | | |
| Oregano (*Origanum* spp.) | | | |
| Allspice (*Pimenta officinalis*) | | | |
| Anise (*Pimpinella anisum*) | | | |
| Angelica Oil (*Angelica* spp.) | a | 1–5 gpa | 3–7 |
| Mustard (*Brassica* spp.) | b | 1–4 qt/a | 2–4 |
| Sage (*Salvia officinalis*) | f | — | 1 |
| Ginger (*Zingiber officinale*) | | | |
| Rose Oil (*Rosa* spp.) | | | |
| Bergamot (*Citrus aurantium bergamia*) | | | |

43
-continued

| Crop | Product | Rate | Applications |
|---|---|---|---|
| Camphor | | | |
| (Cinnamomum camphora) | | | |
| Cananga | | | |
| (Canangium odoratum) | | | |
| Citronella Grass | | | |
| (Cymbopogon nardus) | | | |
| Eucalyptus | | | |
| (Eucalyptus citriodora) | | | |
| Geranium Oil | | | |
| (Perlargonium spp.) | | | |
| Lavandula | | | |
| (Lavandula officinalis) | | | |
| Rosemary | | | |
| (Rosmarinus officinalis) | | | |
| Thyme (Thymus spp.) | | | |
| Turpentine (Pinus spp.) | | | |
| Ornamentals, Forest and Fiber Crops: | | | |
| Cotton | | | |
| (Gossypium spp.) | | | |
| Flax | | | |
| (Linum usitatissimum) | | | |
| Hemp (Canabis sativa) | | | |
| Christmas Trees (various conifers) | | | |
| Ornamental Evergreens | a | 1–5 gpa | 3–10 |
| Rose (Rosa spp.) | b | 1–4 qt/a | 2–4 |
| Chrysanthemum | f | — | 1 |
| (Chrysanthemum spp.) | | | |
| Carnation (Dianthus spp.) | | | |
| (or as root dip) | | | |
| Iris (Iris spp.) | | | |
| Azalea and Rhododendron | | | |
| (Azalea spp.) | | | |
| Houseplants (various species) | | | |

It will therefore be apparent that a novel composition of matter for and a novel method of treating a variety of plants to improve such things as growth, crop yield, resistance to pests and resistance to frost have been provided.

What is claimed is:

1. A aqueous composition of matter for stimulating the growth of plants, said composition comprising:

a carbon/skeleton energy component;

a macronutrient component having at least one water soluble nitrogen source and at least one water soluble phosphorous source; and a vitamin/cofactor component;

in relative amounts effective for stimulating the growth of plants to which the aqueous component is applied.

2. The composition according to claim 1, further comprising a complexing agent.

3. The composition according to claim 2, wherein said complexing agent is selected from the group consisting of sodium lignosulfonate, potassium lignosulfonate, calcium lignosulfonate and calcium lignosulfonate and mixtures thereof.

4. An aqueous composition of matter which is suitable for use as a foliar spray for plants, the aqueous composition comprising:

from about 0.625 to about 8.785 weight percent, based upon the weight of the composition, of a carbon skeleton/energy component selected from the group consisting of water soluble mannose, lactose, dextrose, arythrose, fructose, fucose, galactose, glucose, gulose, maltose, polysaccharides, raffinose, ribose, ribulose, rutinose, saccharose, stachyose, trehalose, xylose, xylulose, adenose, amylose, arabinose, fructose phosphate, fucose-p, galactose-p, glucose-p, lactose-p, maltose-p, mannose-p, ribose-p, ribulose-p, xylose-p, xylulose-p, deoxyribose, adonitol, galactitol, glucitol, maltitol, mannitol-p, ribitol, sorbitol, sorbitol-p, sylitol and mixtures thereof, a macronutrient component having at least one water soluble nitrogen source and at least one water soluble phosphorus source, the macronutrient component being present in an amount effective for providing from about 0.0075 to about 0.625 weight percent, based upon the weight of the composition, nitrogen and from about 0.005 to about 0.625 weight percent, based upon the weight of the composition, phosphorus, the nitrogen source being selected from the group consisting of ammonia, urea, ammonium salts, nitrates, amino acids, proteins, nucleic acids and mixtures thereof, the phosphorus source selected from the group consisting of phosphoric acid, single, double and triple superphosphates, salts of phosphoric acid, nitric acid phosphates and mixtures thereof; and from about 0.00025 to about 0.125 weight percent, based upon the weight of the composition, of a vitamin/cofactor component selected from the group consisting of thiamine, riboflavin, nicotinic acid, pyridoxine, folic acid, biotin, pantothenic acid, cyanocobalamin, phosphatidylcholine, inositol, para-aminobenzoic acid and mixtures thereof, the vitamin/cofactor being in an amount effective for stimulating energy production and biosynthesis by the plant such that the burden of energy production and carbon skeleton production by the carbon skeleton/energy component is shared by photosynthesis and other biosynthetic paths of the plants, the amount of the vitamin/cofactor component being consistent with metabolism and biosynthesis of the plant, the carbon skeleton/energy component being present in substantially greater amount than the macronutrient component and the vitamin/cofactor component.

5. The composition as recited in claim 4 wherein the source of the skeleton/energy component includes molasses.

6. The composition as recited in claim 4 which further comprises a complexing agent in an amount effective for facilitating the transfer of the carbon skeleton/energy component and macronutrient component into the cell structure of the plants.

7. The composition as recited in claim 5 which further comprises a complexing agent in an amount effective for facilitating the transfer of the carbon skeleton/energy component and macronutrient component into the cell structure of the plants.

8. The composition as recited in claim 4 wherein the macronutrient component includes from about 0.0075 to about 0.5625 weight percent water soluble, plant assimilable potassium, from about 0.0025 to about 0.625 weight percent water soluble, plant assimilable calcium, from about 0.00125 to about 0.1875 weight percent water soluble, plant assimilable magnesium and from about 0.0025 to about 0.625 weight percent water soluble, plant assimilable sulfur, and the composition further includes a micronutrient component, the micronutrient component comprising from about 0.00025 to about 0.0125 weight percent water soluble, plant assimilable copper, from about 0.0001 to about 0.00625 weight percent water soluble, plant assimilable boron, from about 0.000025 to about 0.0025 weight percent water soluble, plant assimilable molybdenum and from about 0.000025 to about 0.0025 weight percent water soluble, plant assimilable cobalt.

9. The composition as recited in claim 5 wherein the macronutrient component includes from about 0.0075 to about 0.5625 weight percent water soluble, plant assimilable potassium, from about 0.0025 to about 0.625 weight percent water soluble, plant assimilable calcium, from about 0.00125 to about 0.1875 weight percent water soluble, plant assimilable magnesium and from about 0.0025 to about 0.625 weight percent water soluble, plant assimilable sulfur, and the composition further includes a micronutrient component, the micronutrient component comprising from about 0.00025 to about 0.0125 weight percent water soluble, plant assimilable copper, from about 0.0001 to about 0.00625 weight percent water soluble, plant assimilable boron, from about 0.000025 to about 0.0025 weight percent water soluble, plant assimilable molybdenum and from about 0.000025 to about 0.0025 weight percent water soluble, plant assimilable cobalt.

10. The composition as recited in claims 4 or 5 wherein the macronutrient component includes trivalent nitrogen and pentavalent nitrogen.

11. The composition as recited in claim 10 which further comprises a complexing agent in an amount effective for facilitating the transfer of the carbon skeleton/energy component and macronutrient component into the cell structure of the plants.

12. The composition as recited in claim 11 wherein the macronutrient component includes from about 0.0075 to about 0.5625 weight percent water soluble, plant assimilable potassium, from about 0.0025 to about 0.625 weight percent water soluble, plant assimilable calcium, from about 0.00125 to about 0.1875 weight percent water soluble, plant assimilable magnesium and from about 0.0025 to about 0.625 weight percent water soluble, plant assimilable sulfur, and the composition further includes a micronutrient component, the micronutrient component comprising from about 0.00025 to about 0.0125 weight percent water soluble, plant assimilable copper, from about 0.0001 to about 0.00625 weight percent water soluble, plant assimilable boron, from about 0.000025 to about 0.0025 weight percent water soluble, plant assimilable molybdenum and from about 0.000025 to about 0.0025 weight percent water soluble, plant assimilable cobalt.

13. An aqueous composition of matter which is suitable for use as a foliar spray for plants, the aqueous composition comprising:

from about 0.625 to about 8.785 weight percent, based upon the weight of the composition, molasses;

a macronutrient component having at least one water soluble nitrogen source and at least one water soluble phosphorus source, the macronutrient component being present in an amount effective for providing from about 0.0075 to about 0.625 weight percent, based upon the weight of the composition, nitrogen and from about 0.005 to about 0.625 weight percent, based upon the weight of the composition, phosphorus, the nitrogen source being selected from the group consisting of ammonia, urea, ammonium salts and mixtures thereof, and wherein the phosphorus source includes phosphoric acid; and from about 0.00025 to about 0.125 weight percent, based upon the weight of the composition, of a vitamin/cofactor component selected from the group consisting of thiamine, riboflavin, folic acid and mixtures thereof, the vitamin/cofactor being in an amount effective for stimulating energy production and biosynthesis by the plant such that the burden of energy production and carbon skeleton production by the carbon skeleton/energy component is shared by photosynthesis and other biosynthetic paths of the plants, the amount of the vitamin/cofactor component being consistent with metabolism and biosynthesis of the plant, the carbon skeleton/energy component being present in a greater amount than the macronutrient component and the vitamin/cofactor component.

14. The composition as recited in claim 13 which further comprises a complexing agent in an amount effective for facilitating the transfer of the carbon skeleton/energy component and macronutrient component into the cell structure of the plants.

15. The composition as recited in claim 14 wherein the macronutrient component includes from about 0.0075 to about 0.5625 weight percent water soluble, plant assimilable potassium, from about 0.0025 to about 0.625 weight percent water soluble, plant assimilable calcium, from about 0.00125 to about 0.1875 weight percent water soluble, plant assimilable magnesium and from about 0.0025 to about 0.625 weight percent water soluble, plant assimilable sulfur, and the composition further includes a micronutrient component, the micronutrient component comprising from about 0.00025 to about 0.0125 weight percent water soluble, plant assimilable copper, from about 0.0001 to about 0.00625 weight percent water soluble, plant assimilable boron, from about 0.000025 to about 0.0025 weight percent water soluble, plant assimilable molybdenum and from about 0.000025 to about 0.0025 weight percent water soluble, plant assimilable cobalt.

16. The composition as recited in claims 13, 14 or 15 wherein the macronutrient component includes trivalent nitrogen and pentavalent nitrogen in a ratio in the range of from about 10 moles of trivalent nitrogen to about 90 moles of pentavalent nitrogen to about 90 moles of trivalent nitrogen to about 10 moles of pentavalent nitrogen.

17. An aqueous composition of matter which is suitable for use as a foliar spray for plants, the aqueous composition comprising:

from about 0.625 to about 8.785 weight percent, based upon the weight of the composition, molasses;

a macronutrient component having at least one water soluble nitrogen source and at least one water soluble phosphorus source, the macronutrient component being present in an amount effective for providing from about 0.0075 to about 0.625 weight percent, based upon the weight of the composition, nitrogen and from about 0.005 to about 0.625 weight percent, based upon the weight of the composition, phosphorus, the nitrogen source being selected from the group consisting of ammonia, urea, ammonium salts and mixtures thereof, and wherein the phosphorus source includes phosphoric acid;

from about 0.00025 to about 0.125 weight percent, based upon the weight of the composition, of a vitamin/cofactor component selected from the group consisting of thiamine, riboflavin, folic acid and mixtures thereof, the vitamin/cofactor being in an amount effective for stimulating energy production and biosynthesis by the plant such that the burden of energy production and carbon skeleton production by the carbon skeleton/energy component is shared by photosynthesis and other biosynthetic paths of the plants, the amount of the vitamin/cofactor component being consistent with metabolism and biosynthesis of the plant; and a complexing agent in an amount effective for facilitating the transfer of the carbon skeleton/energy component and macronutrient component into the cell structure of the plants, the complexing agent selected from the group consisting of sodium lignosulfonate, ammonium lignosulfonate, potassium lignosulfonate, calcium lignosulfonate and mixtures thereof, the carbon skeleton/energy component being present in a greater amount than the macronutrient component and the vitamin/cofactor component.

18. The composition as recited in claim 17 wherein the macronutrient component includes trivalent nitrogen and pentavalent nitrogen in a ratio in the range of from about 10 moles of trivalent nitrogen to about 90 moles of pentavalent nitrogen to about 90 moles of trivalent nitrogen to about 10 moles of pentavalent nitrogen.

19. The composition as recited in claim 17 wherein the macronutrient component includes from about 0.0075 to about 0.5625 weight percent water soluble, plant assimilable potassium, from about 0.0025 to about 0.625 weight percent water soluble, plant assimilable calcium, from about 0.00125 to about 0.1875 weight percent water soluble, plant assimilable magnesium and from about 0.0025 to about 0.625 weight percent water soluble, plant assimilable sulfur, and the composition further includes a micronutrient component, the micronutrient component comprising from about 0.00025 to about 0.0125 weight percent water soluble, plant assimilable copper, from about 0.0001 to about 0.00625 weight percent water soluble, plant assimilable boron, from about 0.000025 to about 0.0025 weight percent water soluble, plant assimilable molybdenum and from about 0.000025 to about 0.0025 weight percent water soluble, plant assimilable cobalt.

20. A composition of matter which when diluted with water is suitable for use as a foliar spray for plants, the aqueous composition comprising:

from about 25 to about 70 weight percent, based upon the weight of the composition, molasses;

a macronutrient component having at least one water soluble nitrogen source and at least one water soluble phosphorus source, the macronutrient component being present in an amount effective for providing from about 0.3 to about 5 weight percent, based upon the weight of the composition, nitrogen and from about 0.2 to about 5 weight percent, based upon the weight of the composition, phosphorus, the nitrogen source being selected from the group consisting of ammonia, urea, ammonium salts and mixtures thereof, and wherein the phosphorus source includes phosphoric acid;

from about 0.01 to about 1 weight percent, based upon the weight of the composition, of a vitamin/cofactor component selected from the group consisting of thiamine, riboflavin, folic acid and mixtures thereof, the vitamin/cofactor being in an amount effective for stimulating energy production and biosynthesis by the plant such that the burden of energy production and carbon skeleton production by the carbon skeleton/energy component is shared by photosynthesis and other biosynthetic paths of the plants, the amount of the vitamin/cofactor component being consistent with metabolism and biosynthesis of the plant; and a complexing agent in an amount effective for facilitating the transfer of the carbon skeleton/energy component and macronutrient component into the cell structure of the plants, the complexing agent selected from the group consisting of sodium lignosulfonate, ammonium lignosulfonate, potassium lignosulfonate, calcium lignosulfonate and mixtures thereof, the carbon skeleton/energy component being present in a greater amount than the macronutrient component and the vitamin/cofactor component.

21. A method for assisting the growth of a foliar plant, the method comprising applying to the plant a composition comprising:

from about 0.625 to about 8.785 weight percent, based upon the weight of the composition, of a carbon skeleton/energy component selected from the group consisting of water soluble mannose, lactose, dextrose, arythrose, fructose, fucose, galactose, glucose, gulose, maltose, polysaccharides, raffinose, ribose, ribulose, rutinose, saccharose, stachyose, trehalose, xylose, xylulose, adenose, amylose, arabinose, fructose phosphate, fucos-p, galactose-p, glucose-p, lactose-p, maltose-p, mannose-p, ribose-p, ribulose-p, xylose-p, xylulose-p, deoxyribose, adonitol, galactitol, glucitol, maltitol, mannitol-p, ribitol, sorbitol, sorbitol-p, sylitol and mixtures thereof;

a macronutrient component having at least one water soluble nitrogen source and at least one water soluble phosphorus source, the macronutrient component being present in an amount effective for providing from about 0.0075 to about 0.625 weight percent, based upon the weight of the composition, nitrogen and from about 0.005 to about 0.625 weight percent, based upon the weight of the composition, phosphorus, the nitrogen source being selected from the group consisting of ammonia, urea, ammonium salts, nitrates, amino acids, proteins, nucleic acids and mixtures thereof, the phosphorus source selected from the group consisting of phosphoric acid, single, double and triple superphosphates, salts of phosphoric acid, nitric acid phosphates and mixtures thereof; and from about 0.00025 to about 0.125 weight percent, based upon the weight of the composition, of a vitamin/cofactor component selected from the group consisting of thiamine, riboflavin, nicotinic acid, pyridoxine, folic acid, biotin, pantothenic acid, cyanocobalamin, phosphatidylcholine, inositol, para-aminobenzoic acid and mixtures thereof, the vitamin/cofactor being in an amount effective for stimulating energy production and biosynthesis by the plant such that the burden of energy production and carbon skeleton production by the carbon skeleton/energy component is shared by photosynthesis and other biosynthetic paths of the plants, the amount of the vitamin/cofactor component being consistent with metabolism and biosynthesis of the plant, the carbon skeleton/energy component being present in substantially greater amount than the macronutrient component and the vitamin/cofactor component.

22. A method for promoting growth of a foliar plant and offsetting the adverse affect on a foliar plant by nematodes, the method comprising applying to the plant and the soil around the plant a composition comprising:

from about 0.625 to about 8.785 weight percent, based upon the weight of the composition, molasses;

a macronutrient component having at least one water soluble nitrogen source and at least one water soluble phosphorus source, the macronutrient component being present in an amount effective for providing from about 0.0075 to about 0.625 weight percent, based upon the weight of the composition, nitrogen and from about 0.005 to about 0.625 weight percent, based upon the weight of the composition, phosphorus, the nitrogen source being selected from the group consisting of ammonia, urea, ammonium salts and mixtures thereof, and wherein the phosphorus source includes phosphoric acid;

from about 0.00025 to about 0.125 weight percent, based upon the weight of the composition, of a vitamin/cofactor component selected from the group consisting of thiamine, riboflavin, folic acid and mixtures thereof, the vitamin/cofactor being in an amount effective for stimulating energy production and biosynthesis by the plant such that the burden of energy production and carbon skeleton production by the carbon skeleton/ energy component is shared by photosynthesis and other biosynthetic paths of the plants, the amount of the vitamin/cofactor component being consistent with metabolism and biosynthesis of the plant; and a complexing agent in an amount effective for facilitating the transfer of the carbon skeleton/energy component and macronutrient component into the cell structure of the plants, the complexing agent selected from the group consisting of sodium lignosulfonate, ammonium lignosulfonate, potassium lignosulfonate, calcium lignosulfonate and mixtures thereof, the carbon skeleton/energy component being present in a greater amount than the macronutrient component and the vitamin/cofactor component.

23. A method for promoting growth of a foliar plant and offsetting the adverse affect on a foliar plant by nematodes as recited in claim 22 wherein the macronutrient component includes trivalent nitrogen and pentavalent nitrogen in a ratio in the range of from about 10 moles of trivalent nitrogen to about 90 moles of pentavalent nitrogen to about 90 moles of trivalent nitrogen to about 10 moles of pentavalent nitrogen.

24. The method for promoting growth of a foliar plant and offsetting the adverse affect on a foliar plant by nematodes as recited in claim 23 wherein the macronutrient component includes from about 0.0075 to about 0.5625 weight percent water soluble, plant assimilable potassium, from about 0.0025 to about 0.625 weight percent water soluble, plant assimilable calcium, from about 0.00125 to about 0.1875 weight percent water soluble, plant assimilable magnesium and from about 0.0025 to about 0.625 weight percent water soluble, plant assimilable sulfur, and the composition further includes a micronutrient component, the micronutrient component comprising from about 0.00025 to about 0.0125 weight percent water soluble, plant assimilable copper, from about 0.0001 to about 0.00625 weight percent water soluble, plant assimilable boron, from about 0.000025 to about 0.0025 weight percent water soluble, plant assimilable molybdenum and from about 0.000025 to about 0.0025 weight percent water soluble, plant assimilable cobalt.

* * * * *